US007887809B1

(12) United States Patent
Garen et al.

(10) Patent No.: US 7,887,809 B1
(45) Date of Patent: Feb. 15, 2011

(54) NEOVASCULAR-TARGETED IMMUNOCONJUGATES

(75) Inventors: Alan Garen, New Haven, CT (US); Zhiwei Hu, New Haven, CT (US)

(73) Assignee: Yale University, New Haven, CT (US)

( * ) Notice: Subject to any disclaimer, the term of this patent is extended or adjusted under 35 U.S.C. 154(b) by 443 days.

(21) Appl. No.: 11/925,007

(22) Filed: Oct. 26, 2007

Related U.S. Application Data

(60) Continuation of application No. 11/134,428, filed on May 23, 2005, now Pat. No. 7,858,092, which is a division of application No. 10/030,203, filed as application No. PCT/US00/16481 on Jun. 14, 2000, now Pat. No. 6,924,359.

(60) Provisional application No. 60/142,161, filed on Jul. 1, 1999.

(51) Int. Cl.
*A61K 39/00* (2006.01)

(52) U.S. Cl. ............... 424/182.1; 424/178.1; 514/2; 530/384; 530/387.1; 530/387.3; 530/391.7

(58) Field of Classification Search ............. 424/178.1, 424/182.1; 514/2; 530/384, 387.1, 387.3, 530/391.7
See application file for complete search history.

(56) References Cited

U.S. PATENT DOCUMENTS

| 4,752,569 | A | 6/1988 | Terasaki et al. |
|---|---|---|---|
| 4,865,998 | A | 9/1989 | Feickert et al. |
| 4,997,762 | A | 3/1991 | Hanna, Jr. et al. |
| 5,091,513 | A | 2/1992 | Huston et al. |
| 5,605,690 | A | 2/1997 | Jacobs et al. |
| 5,759,808 | A | 6/1998 | Casterman et al. |
| 5,800,988 | A | 9/1998 | Casterman et al. |
| 5,840,526 | A | 11/1998 | Casterman et al. |
| 5,877,289 | A | 3/1999 | Thorpe et al. |
| 5,879,672 | A | 3/1999 | Davis et al. |
| 5,939,530 | A | 8/1999 | Gelboin et al. |
| 5,969,107 | A | 10/1999 | Carceller et al. |
| 5,981,471 | A | 11/1999 | Papathanasiu et al. |
| 6,001,978 | A | 12/1999 | Edgington et al. |
| 6,005,079 | A | 12/1999 | Casterman et al. |
| 6,015,695 | A | 1/2000 | Casterman et al. |
| 6,017,514 | A | 1/2000 | Epstein et al. |
| 6,132,729 | A | 10/2000 | Thorpe et al. |
| 6,140,470 | A | 10/2000 | Garen et al. |
| 6,342,219 | B1 | 1/2002 | Thorpe et al. |
| 6,406,697 | B1 | 6/2002 | Capon et al. |
| 6,448,071 | B1 | 9/2002 | Schneck et al. |
| 6,541,610 | B1 | 4/2003 | Smith |
| 6,555,319 | B2 | 4/2003 | Wong et al. |
| 6,572,852 | B2 | 6/2003 | Smith et al. |

FOREIGN PATENT DOCUMENTS

WO WO-96/01653 A 1/1996

WO WO-98/31394 A 7/1998

OTHER PUBLICATIONS

Kimura et al., "The Potential of Active Drug Targeting with Immunoconjugates to Choroidal Neovascularization", IOVS, vol. 41, No. 4, Mar. 15, 2000, p. S180.
Gewolb, J. "New Cancer Therapy Kills Blood Vessels," *Science On Line*, Oct. 1, 2001. http://www.iconictherapeutics.com/SCIENCE01.pdf.
"Molecule May Kill Cancer Tumors," *The Associated Press*, Oct. 1, 2001. http://www.iconictherapeutics.com/APx01.pdf.
Schubert, Charlotte. "Meddling in macular degeneration," *Nature Medicine*, Apr. 2003. vol. 9, No. 4, p. 396.
Usman et al. (2001), "Hypocholesterolemic effect of *Lactobacillus gasseri* SBT0270 in rats fed a cholesterol-enriched diet", *J. Dairy Res.*, 68: 617-624.
Zhou et al. (2000), "Safety assessment of potential probiotic lactic acid bacterial strains *Lactobacillus rhamnosus* HN001, *Lb. acidophilus* HN017, and *Bifidobacterium lactis* HN019 in BALB/c mice", *International Journal of Food Microbiology*, 56: 87-96.
Agerholm-Larsen et al. (2000), "Effect of 8 week intake of probiotic milk products on risk factors for cardiovascular diseases", *Eur J Clin Nutr.*, 54(4): 288-97.
Gordon et al. (1989), "High-Density Lipoprotein Cholesterol and Cardiovascular Disease", *Circulation*, 79:8-15.
Peppel et al., "A tumor necrosis factor (TNF) receptor-IgG heavy chain chimeric protein as a bivalent antagonist of TNF activity", *J. Exp. Med.*, Dec. 1991, pp. 1483-1489, vol. 174, No. 6. (Abstract only).
E. Wilmes et al., "Versuche zur Herstellung menschlicher monoklonaler Antikorper gegen Melanome unter Verwendung zervikaler Lymphknoten," *Laryng. Rhinol. Otol.*, (1987), vol. 66, pp. 144-148.
Jamie K. Scott and George Smith, "Searching for Peptide Ligands with an Epitope Library," *Science*, (Jul. 27, 1990), vol. 249, pp. 386-390.
James D. Marks et al., "By-passing Immunization Human Antibodies from V-gene Libraries Displayed on Phage," *J. Med Biol.*, (1991), vol. 222, pp. 581-597.

(Continued)

*Primary Examiner*—Stephen L Rawlings
*Assistant Examiner*—Brad Duffy
(74) *Attorney, Agent, or Firm*—Banner & Witcoff, Ltd.

(57) ABSTRACT

Immunoconjugates for treating diseases associated with neovascularization such as cancer, rheumatoid arthritis, the exudative form of macular degeneration, and atherosclerosis are described. The immunoconjugates typically consist of the Fc region of a human IgG1 immunoglobulin including the hinge, or other effector domain or domains that can elicit, when administered to a patient, a cytolytic immune response or cytotoxic effect against a targeted cell. The effector domain is conjugated to a targeting domain which comprises a factor VII mutant that binds with high affinity and specificity to tissue factor but does not initiate blood clotting such as factor VII having a substitution of alanine for lysine-341 or of alanine for serine-344.

4 Claims, 16 Drawing Sheets

OTHER PUBLICATIONS

Greg Winter and Cesar Milstein, "Man-made Antibodies," *Nature*, (Jan. 24, 1991), vol. 349, pp. 293-299.

James D. Marks et al., By-passing Immunization: Building High Affinity Human Antibodies by Chain Shuffling, *Bio/Technology*, (Jul. 1992), vol. 10, pp. 779-783.

G. Del Bino et al., "Apoptotic Cell Death Triggered by Camptothecin or Tenipos.de. The Cell Cycle Specificity and Effects of Ionizing Radiation," *Cell Prolif.*, (1992), vol. 25, pp. 537-548.

Andrew D. Griffiths et al., "Human Anti-self Antibodies with High Specificity from Phage Display Libraries," *The EMBO Journal*, (1993), vol. 12, No. 2, pp. 725-734.

Lee H. Pai and Ira Pastan, "Immunotoxin Therapy for Cancer," *JAMA*, (Jan. 6, 1993), vol. 269, No. 1, pp. 78-81.

Dave S.B. Hoon et al., "Molecular Cloning of a Human Monoclonal Antibody Reactive to Ganglioside Antigen on Human Cancers," *Cancer Research*, (Nov. 1, 1993), vol. 53, pp. 5244-5250.

Maria-Ana Ghetie and Ellen S. Vitetta, "Recent Developments in ImmunotoxinTherapy," *Current Opinion in Immunology*, (1994), vol. 6, pp. 707-714.

Brenda L. Hall et al., "Establishment, Molecular Rescue, and Expression of 123AV16-1, a Tumor-reactive Human Monoclonal Antibody," *Cancer Research*, (1994), vol. 54, pp. 5178-5185.

Xiaohong Cai and Alan Garen, "Anti-melanoma Antibodies from Melanoma Patients Immunized with Genetically Modified Autologous tumor cells: Selection of Specific Antibodies from Single-Chain Fv Phage Fusion Libraries,"*Proc. Natl. Acad. Sci. USA*, (1995), vol. 92, pp. 6537-6541.

Martin Friedlander et al., "Involvement of Integrins $\alpha_v\beta_3$ and $\alpha_v\beta_5$ in Ocular Neovascular Diseases," *Proc. Natl. Acad. Sci. USA*, (Sep. 1996), vol. 93, pp. 9764-9769.

Xiaohong Cai and Alan Garen, "A Melanoma-Specific $V_H$ Antibody Cloned from a Fusion Phage Library of a Vaccinated Melanoma Patient," *Proc. Natl. Acad. Sci. USA*, (Jun. 1996), vol. 93, pp. 6280-6285.

Craig D. Dickinson, "Identification of Surface Residues Mediating Tissue Factor Binding and Catalytic Function of the Serine Protease Factor Vlla", Proc. Natl. Acad. Sci USA, (Dec. 1996), vol. 93, pp. 14379-14384.

Xiaohong Cai and Alan Garen, "Comparison of Fusion Phage Libraries Displaying VH or Single-chain Fv Antibody Fragments Derived from the Antibody Reportoire of a Vaccinated Melanoma Patient as a Source of Melanoma-Specific Targeting Molecules," Proc. Natl. Acad. Sci. USA, (Aug. 1997), vol. 94, pp. 9261-9266.

Hennie R. Hoogenboom, "Designing and Optimizing Library Selection Strategies for Generating High-affinity Antibodies," Tibtech, (Feb. 1997), vol. 15, pp. 62-70.

Baiyang Wang, et al, "Human Single-chain Fv Immunoconjugates Targeted to a Melanoma-associated Chondroitin Sulfate Proteoglycan Mediate Specific Lysis of Human Melanoma Cells by Natural Killer Cells and Complement," Proc. Natl. Acad. Sci. USA, (Feb. 1999), vol. 96, pp. 1627-1632.

DJ Chaplin and GJ Dougherty, "Tumour Vasculature as a Target for Cancer Therapy," British Journal of Cancer, (1999), vol. 80 (Supplement 1), pp. 57-64.

Zoltan Szekanecz et al., "Angiogenesis in Rheumatoid Arthritis: Pathogenic and Clinical Significance," J Investig. Med., (1998), vol. 46, pp. 27-41.

Gary S. Firestein, "Starving the Synovium: Angiogenesis and Inflammation in Rheumatoid Arthritis," The Journal of Clinical Investigation, (Jan. 1999), vol. 103, No. 1, pp. 3-4.

Chris M. Storgard et al., "Decreased Angiogenesis and Arthritic Disease in Rabbits Treated with an $\alpha v\beta_3$ Antagonist," *The Journal of Clinical Investigation*, (1999), vol. 103, No. 1, pp. 47-54.

Henry J. Kaplan et al., "Fas Ligand (CD95 Ligand) Controls Angiogenesis Beneath the Retina," *Nature Medicine*, (Mar. 1999), vol. 5, No. 3, pp. 292-297.

Glenn Dranoff and Richard C. Mulligan, "Gene Transfer as Cancer Therapy," *Advances in Immunology*, vol. 58, (1995), pp. 417-454.

E. Haber and F.F. Richards, "The Specificity of Antigenic Recognition of Antibody Heavy Chain," Proc. R. Soc. Lond. B. Biol. Sci., (1996), vol. 166, pp. 176-187.

Zhiwei Hu and Alan Garen, "Intratumoral Injection of Adenoviral Vectors Encoding Tumor-targeted Immunoconjugates for Cancer Immunotherapy," *Proc. Natl. Acad. Sci.*, (Aug. 1, 2000), vol. 97, No. 16, pp. 9221-9225.

Zhiwei Hu, et al, "Targeting Tissue Factor on Tumor Vascular Endothelial Cells and Tumor Cells for Immunotherapy in Mouse Models of Prostatic Cancer", *Proc. Natl. Acad. Sci.*, (Oct. 9, 2001), vol. 98, No. 21, pp. 12180-12185.

Puran S. Bora, et al., "Immunotherapy for Choroidal Neovascularization of a Laser-induced Mouse Model Simulating Exudative (wet) Macular Degeneration,"*Proc. Natl. Acad. Sci.*, Proc. Natl. Acad. Sci. USA, (Mar. 4, 2003), vol. 100, No. 5, pp. 2579-2684.

Dal Porto et al., "A soluble divalent class I major hisocompatibility compelx molecule inhibits alloreactive T cells at nanomolar concentrations", *Proc. Natl., Acad. Sci USA*, Jul. 1993, pp. 6671-6675, vol. 90.

Eilat et al., "Secretion of a soluble, chimeric γδ T-cell receptor-immunoglobulin heterodimer", *Proc. Natl. Acad. Sci. USA*, Aug. 1992, pp. 6871-6875, vol. 89.

Grégoire et al., "Engineered secreted T-cell receptor $\alpha\beta$ heterodimers", *Proc. Natl. Acad. Sci. USA*, Sep. 1991, pp. 8077-8081, vol. 88.

Mohler et al., "Soluble Tumor Necrosis Factor (TNF) Receptors Are Effective Therapeutic Agents in Lethal Endotoxemia and Function Simultaneously as Both TNF Carriers and TNF Antagonists", *J. Immunol.*, Aug. 1993, pp. 1548-1561, vol. 151, No. 3.

Erben et al., "Differential effects of a stem cell factor-immunoglobulin fusion protein on malignant and normal hematopoietic cells", *Cancer Res.*, Jun. 1999, pp. 2924-2930, vol. 59, No. 12 (Abstract only).

Baba, E., "Effects of IgC-Fc-mitomycin C conjugate on cancer cells", *Hokkaido Igaku Zasshi*, Mar. 1996, pp. 271-281, vol. 71, No. 2 (Article in Japanese; abstract only).

Nakagaki et al. Biochemistry, 30(45):10819-10824, 1991.

Olson et al. International Journal of Cancer, 73:865-870, 1997.

Drake et al. American Journal of Pathobiology, 134(5): 1087-1097, 1989.

Contrino et al. Nature Medicine, 2:209-215, 1996.

Dickinson et al. Proc. Natl. Acad. Sci, USA, 93:14379-14384, 1996.

Min et al. Cancer Research, 56:2428-2432, 1996.

Cruse et al. Illustrated Dictionary of Immunology, CRC Press, p. 109, 1995.

Rudikoff et al. Proc. Natl. Acad. Sci. USA, 79:1979-1983, 1982.

Lederman et al. Molecular Immunology 28:1171-1181, 1991.

Li et al. Proc. Natl. Acad. Sci. USA 77:3211-3214, 1980.

Coleman P. M. Research in Immunology, 145:33-36, 1994.

Wang et al. PNAS 96:1627-32, 1999.

Mori et al. Investigative Ophthalmology and Visual Science, 43(7):2428-2434, Jul. 2002.

Tosatto et al. Current Pharmaceutical Design, 12(17):2067-2086, 2006.

Dennis, Nature,442:739-741, Aug. 2006.

Srivastava, Nature Immunology, 1(5):363-366, Nov. 2000.

Tarnawski, Digestive Diseases and Sciences, 50:S24-S33, Oct. 2005.

Kijilstra et al., Ocular Immunology and Inflammation, 13:3-11, 2005.

Kelland, European Journal of Cancer, 40:827-836, 2004.

Schwesinger et al., American Journal of Pathology, 158(3):1161-1172, Mar. 2001.

Roodhooft, Bulletin De La Socitie Belge D'Ophtalmologie, 276, 83-92, 2000.

Grossniklaus et al., Molecular Vision, 8:19-126, Apr. 2002.

Kimizuru et al., Investigative Ophthalmology and Visual Science, 42(11):2664:2672, Oct. 2001.

E. Ruoslahti, Nature Reviews, 2:83-90 (2002).

Z. Hu et al., Proc. Natl. Acad. Sci. USA 96:8161-8166.

Muller, et al., "Expression of tissue factor by melanoma cells promotes efficient hematogenous metastasis," Proc. Natl Acad. Sci, USA, 1992, vol. 89, No. 24, pp. 11832-11836.

Fischer, et al., "Tissue Factor-initiated Thrombin Generation Activates the Signaling Thrombin receptor on Malignant Melanoma Cells," Cancer Research, 1995, vol. 55, No. 8, pp. 1629-1632.

Amirkhosravi, et al., "Pentoxifylline Inhibits Hypoxia-induced Upregulation of Tumor Cell Tissue Factor and Vascular Endothelial Growth Factor," Thrombosis and Haemostasis, 1998, vol. 80, No. 4, pp. 598-602.

Shoji, et al., "Activation of Coagulation and Angiognesis in Cancer: Immunohistochemical Localization in Situ of Clotting Proteins and Vascular Endothelial Growth Factor in Human Cancer," American Journal of Pathology, 1998, vol. 152, No. 2, pp. 399-411.

Mueller, et al., "Requirement for Binding of Catalytically Active Factor Vlla in Tissue Factor-dependent Experimental Metastasis," Journal of Clinical Investigation, 1998, vol. 101, No. 7, pp. 1372-1378.

Lin, et al., "Actiangiogenic gene therapy targeting the endothelium-specific receptor tyrosine kinase Tie2," Proc. Natl. Acad. Sci. USA, 1998, vol. 95., No. 15, pp. 8829-8834.

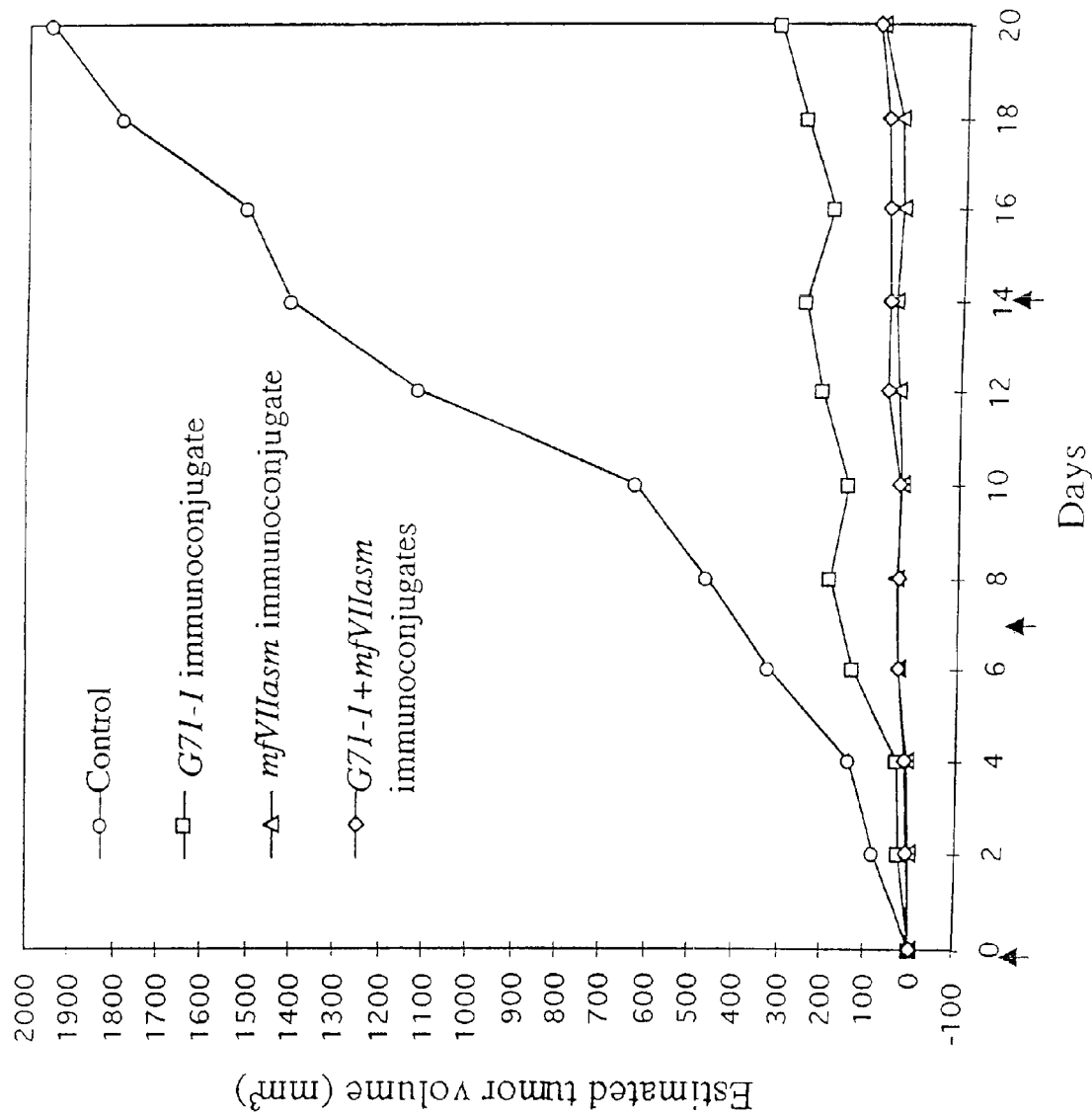

Figure 10A
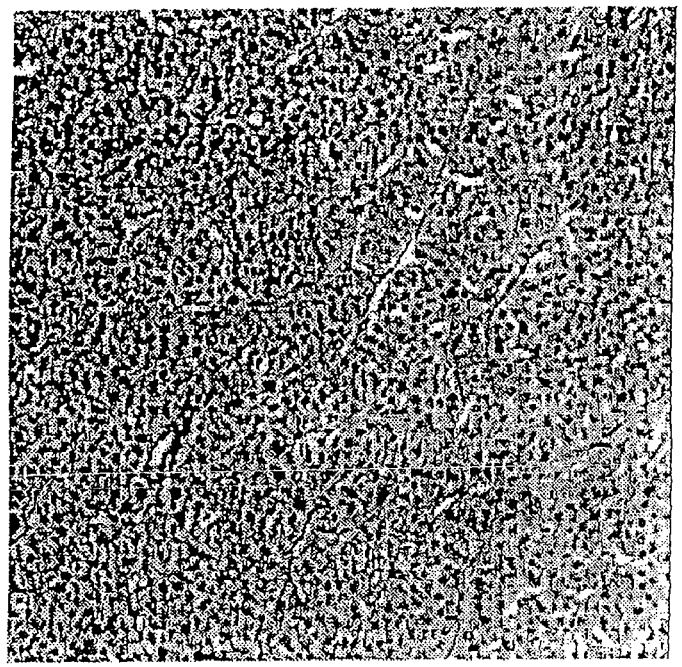
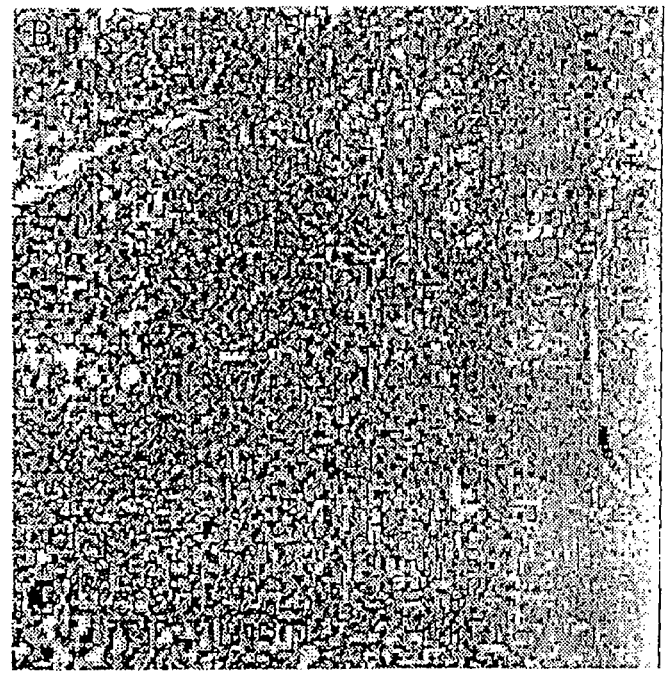
Figure 10B

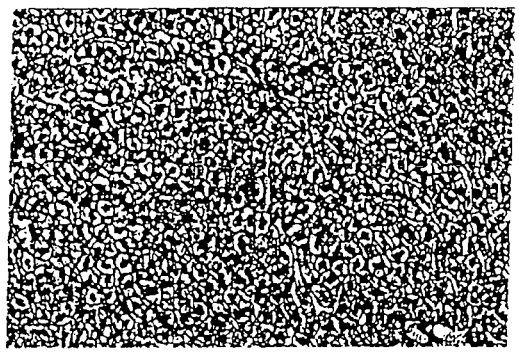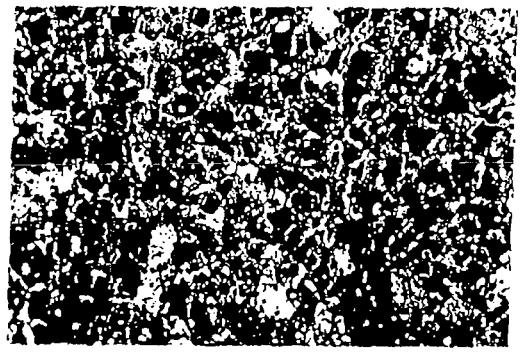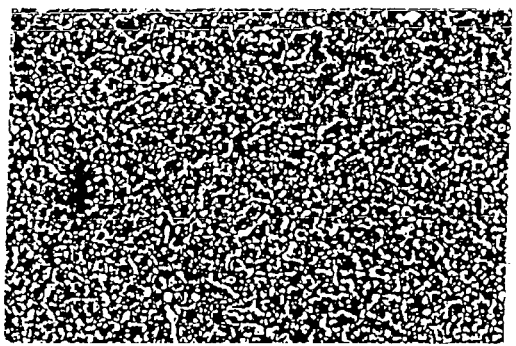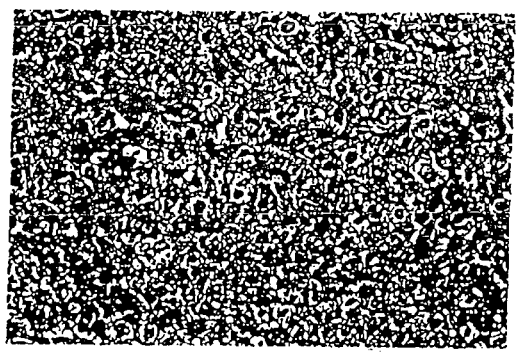
Figure 15

SEQUENCE LISTING

<160> NUMBER OF SEQ ID NOS: 12

<210> SEQ ID NO 1
<211> LENGTH: 60
<212> TYPE: DNA
<213> ORGANISM: Artificial Sequence
<220> FEATURE:
<221> NAME/KEY: primer
<223> OTHER INFORMATION: used in constructs

<400> SEQUENCE: 1
gtcgagcaga gctccaggtg cagctggtgc agtctggggc tgaggtgagg        50
tgaagaagcc                                                    60

<210> SEQ ID NO 2
<211> LENGTH: 39
<212> TYPE: DNA
<213> ORGANISM: Artificial Sequence
<220> FEATURE:
<221> NAME/KEY: primer
<223> OTHER INFORMATION: used in constructs

<400> SEQUENCE: 2
acgttcaggg gatccaccta ggacggtcag cttggtccc                    39

<210> SEQ ID NO 3
<211> LENGTH: 44
<212> TYPE: DNA
<213> ORGANISM: Artificial Sequence
<220> FEATURE:
<221> NAME/KEY: primer
<223> OTHER INFORMATION: used in constructs

<400> SEQUENCE: 3
accttgcagg atccgcaaga cccaaatctt gtgacaaaac tcac              44

<210> SEQ ID NO 4
<211> LENGTH: 50
<212> TYPE: DNA
<213> ORGANISM: Artificial Sequence
<220> FEATURE:
<221> NAME/KEY: primer
<223> OTHER INFORMATION: used in constructs

<400> SEQUENCE: 4
gatcacgtgt cgacttatca tttacccgga gacagggaga ggctcttctg        50

<210> SEQ ID NO 5
<211> LENGTH: 67
<212> TYPE: DNA
<213> ORGANISM: Artificial Sequence
<220> FEATURE:
<221> NAME/KEY: primer
<223> OTHER INFORMATION: used in constructs

<400> SEQUENCE: 5
aattcatgga gtttgggctg agctggcttt ttcttgttgc tgcattaaga        50
ggtgtccagt ccgagct                                            67

<210> SEQ ID NO 6
<211> LENGTH: 57
<212> TYPE: DNA
<213> ORGANISM: Artificial Sequence
<220> FEATURE:

```
<221> NAME/KEY: primer
<223> OTHER INFORMATION: used in constructs

<400> SEQUENCE: 6
cggactggac acctgttaat gcagcaacaa gaaaagccag ctcagcccaa        50
actcatg                                                      57

<210> SEQ ID NO 7
<211> LENGTH: 38
<212> TYPE: DNA
<213> ORGANISM: Artificial Sequence
<220> FEATURE:
<221> NAME/KEY: primer
<223> OTHER INFORMATION: used in constructs

<400> SEQUENCE: 7
acgatcttaa gcttccccac agtctcatca tggttcca                    38

<210> SEQ ID NO 8
<211> LENGTH: 38
<212> TYPE: DNA
<213> ORGANISM: Artificial Sequence
<220> FEATURE:
<221> NAME/KEY: primer
<223> OTHER INFORMATION: used in constructs

<400> SEQUENCE: 8
acggtaacgg atcccagtag tgggagtcgg aaaacccc                    38

<210> SEQ ID NO 9
<211> LENGTH: 39
<212> TYPE: DNA
<213> ORGANISM: Artificial Sequence
<220> FEATURE:
<221> NAME/KEY: primer
<223> OTHER INFORMATION: used in constructs

<400> SEQUENCE: 9
ggtaccaagg acgcctgcgc gggtgacagc ggtggccca                   39

<210> SEQ ID NO 10
<211> LENGTH: 39
<212> TYPE: DNA
<213> ORGANISM: Artificial Sequence
<220> FEATURE:
<221> NAME/KEY: primer
<223> OTHER INFORMATION: used in constructs

<400> SEQUENCE: 10
tgggccaccg ctgtcacccg cgcaggcgtc cttggtacc                   39

<210> SEQ ID NO 11
<211> LENGTH: 1519
<212> TYPE: DNA
<213> ORGANISM: Artificial Sequence
<220> FEATURE:
<221> NAME/KEY: CDS
<223> OTHER INFORMATION: G71-1 immunoconjugate
      includes leader + G71 + linker + VL + IgG1Fc

<400> SEQUENCE: 11
atggagtttg ggctgagctg gcttttttctt gttgctgcat taagaggtgt      50
ccagtccgag ctccaggtgc agctggtgca gtctggggct gaggtgaaga       100
agcctgggtc ctcggtgaag gtctcctgca aggcttctgg aggcaccttc       150
```

-continued

| | |
|---|---|
| agcagctatg ctatcagctg ggtgcgacag gcccctggac aagggcttga | 200 |
| gtggatggga gggatcatcc ctatctttgg tacagcaaac tacgcacaga | 250 |
| agttccaggg cagagtcacg attaccgcgg acaaatccac gagcacagcc | 300 |
| tacatggagc tgagcagcct gagatctgag gacacggccg tgtattactg | 350 |
| tgcgagagga ggagggagat atgatgcttt tgatatctgg ggccaaggaa | 400 |
| aacactggtc accgtctctt caggtggcgg tggctcgggc ggtggtgggt | 450 |
| cgggtggcgg cggatctcag tctgccctga cgcagccgcc ctcggtgtct | 500 |
| gaagccccca gcagaggtc accatctcct gttctggaag cagctccaac | 550 |
| atcggaaata tgctgtaaa ctggtaccag cagctcccag gaaaggctcc | 600 |
| caaactcctc atctattatg gtgatctgct gccctcaggg tctctgaccg | 650 |
| attctctggc tccaagtctg gcacctcagc cttcctggcc atcagtgggc | 700 |
| tccagtctga ggatgaggct tgattattac tgccagtgtt acgacaccag | 750 |
| cctgagtgga gtgctattcg gcggagggcc aagctgcccg tccctaggtg | 800 |
| gatccgcaga gcccaaatct tgtgacaaaa ctcacacatg cccaccgtgc | 850 |
| ccagcacctg aactcctggg gggaccgtca gtcttcctct tccccccaaa | 900 |
| acccaaggac accctcatga tctcccggac ccctgaggtc acatgcgtgg | 950 |
| tggtggacgt gagccacgaa gaccctgagg tcaagttcaa ctggtacgtg | 1000 |
| gacggcgtgg aggtgcataa tgccaagaca aagccgcggg aggagcagta | 1050 |
| caacagcacg taccgtgtgg tcagcgtcct caccgtcctg caccaggact | 1100 |
| ggctgaatgg caaggagtac aagtgcaagg tctccaacaa agccctccca | 1150 |
| gcccccatcg agaaaaacca tctccaaagc caaagggcag ccccgagaac | 1200 |
| cacaggtgta caccctgccc ccatcccggg atgagctgac caagaaccag | 1250 |
| gtcagcctga cctgcctggt caaaggcttc tatcccagcg acatcgccgt | 1300 |
| ggagtgggag agcaatgggc agccggagaa caactacaag accacgcctc | 1350 |
| ccgtgctgga ctccgacggc tccttcttcc tctacagcaa gctcaccgtg | 1400 |
| gacaagagca ggtggcagca ggggaacgtc ttctcatgct ccgtgatgca | 1450 |
| tgaggctctg cacaaccact acaggcagaa gagcctctcc ctgtctccgg | 1500 |
| gtaaatgata agcggccgc | 1519 |

<210> SEQ ID NO 12
<211> LENGTH: 2138
<212> TYPE: DNA
<213> ORGANISM: Artificial Sequence
<220> FEATURE:
<221> NAME/KEY: CDS
<223> OTHER INFORMATION: hfVIIasm immunoconjugate
      includes leader + hfVIIasm + human IgG1Fc

<400> SEQUENCE: 12

| | |
|---|---|
| aagctttgca gagatttcat catggtctcc caggccctca ggctcctctg | 50 |
| ccttctgctt gggcttcagg gctgcctggc tgcaggcggg gtcgctaagg | 100 |
| cctcaggagg agaaacacgg gacatgccgt ggaagccggg gcctcacaga | 150 |
| gtcttcgtaa cccaggagga agcccacggc gtcctgcacc ggcgccggcg | 200 |
| cgccaacgcg ttcctggagg agctgcggcc gggctccctg gagagggagt | 250 |
| gcaaggagga gcagtgctcc ttcgaggagg cccgggagat cttcaaggac | 300 |

-continued

| | |
|---|---|
| gcggagagga cgaagctgtt ctggatttct tacagtgatg gggaccagtg | 350 |
| tgcctcaagt ccatgccaga atgggggctc ctgcaaggac cagctccagt | 400 |
| cctatatctg cttctgcctc cctgccttcg agggccggaa ctgtgagacg | 450 |
| cacaaggatg accagctgat ctgtgtgaac gagaacggcg gctgtgagca | 500 |
| gtactgcagt gacccacacgg gcaccaagcg ctcctgtcgg tgccacgagg | 550 |
| ggtactctct gctggcagac ggggtgtcct gcacacccac agttgaatat | 600 |
| ccatgtggaa aaatacctat tctagaaaaa agaaatgcca gcaaacccca | 650 |
| aggccgaatt gtgggggca aggtgtgccc caaaggggag tgtccatggc | 700 |
| aggtcctgtt gttggtgaat ggagctcagt tgtgtggggg gaccctgatc | 750 |
| aacaccatct gggtggtctc cgcggcccac tgtttcgaca aaatcaagaa | 800 |
| ctggaggaac ctgatcgcgg tgctgggcga gcacgacctc agcgagcacg | 850 |
| acggggatga gcagagccgg cgggtggcgc aggtcatcat ccccagcacg | 900 |
| tacgtcccgg gcaccaccaa ccacgacatc gcgctgctcc gcctgcacca | 950 |
| gcccgtggtc ctcactgacc atgtggtgcc cctctgcctg cccgaacgga | 1000 |
| cgttctctga gaggacgctg gccttcgtgc gcttctcatt ggtcagcggc | 1050 |
| tggggccagc tgctggaccg tggcgccacg gccctggagc tcatggtgct | 1100 |
| caacgtgccc cggctgatga cccaggactg cctgcagcag tcacggaagg | 1150 |
| tgggagactc cccaaatatc acggagtaca tgttctgtgc cggctactcg | 1200 |
| gatggcagca aggactcctg cgcggggga c agtggaggcc cacatgccac | 1250 |
| ccactaccgg ggcacgtggt acctgacggg catcgtcagc tggggccagg | 1300 |
| gctgcgcaac cgtgggccac tttggggtgt acaccagggt ctcccagtac | 1350 |
| atcgagtggc tgcaaaagct catgcgctca gagccacgcc caggagtcct | 1400 |
| cctgcgagcc ccatttcccg gatccgcaga gcccaaatct tgtgacaaaa | 1450 |
| ctcacacatg cccaccgtgc ccagcacctg aactcctggg gggaccgtca | 1500 |
| gtcttcctct tccccccaaa acccaaggac accctcatga tctcccggac | 1550 |
| ccctgaggtc acatgcgtgg tggtggacgt gagccacgaa gaccctgagg | 1600 |
| tcaagttcaa ctggtacgtg gacggcgtgg aggtgcatas tgccaagaca | 1650 |
| aagccgcggg aggagcagta caacagcacg taccgtgtgg tcagcgtcct | 1700 |
| caccgtcctg caccaggact ggctgaatgg caaggagtac aagtgcaagg | 1750 |
| tctccaacaa agccctccca gcccccatcg agaaaaccat ctccaaagcc | 1800 |
| aaagggcagc cccgagaacb acaggtgtac accctgcccc catcccggga | 1850 |
| tgagctgacc aagaaccagg tcagcctgac ctgcctggtc aaaggcttct | 1900 |
| atcccagcga catcgccgtg gagtgggaga gcaatgggca gccggagaac | 1950 |
| aactacaaga ccacgcctcc cgtgctggac tccgacggcc ccttcttcct | 2000 |
| ctacagcaag ctcaccgtgg acaagagcag gtggcagcag gggaacgtct | 2050 |
| tctcatgctc cgtgatgcat gaggctctgc acaaccacta cacgcagaag | 2100 |
| agcctctccc tgtctccggg taaatgataa gcggccgc | 2138 |

NEOVASCULAR-TARGETED IMMUNOCONJUGATES

CROSS-REFERENCES TO RELATED APPLICATIONS

This application claims priority benefit of U.S. Ser. No. 60/142,161, filed Jul. 1, 1999.

STATEMENT REGARDING FEDERALLY SPONSORED RESEARCH

The invention was made with partial government support under Project Grant HL29019-17 from the National Institutes of Health, U.S. Public Health Service. The government has certain rights in the invention.

BACKGROUND OF THE INVENTION

1. Field of the Invention

This invention relates to the design, synthesis, and administration of immunoconjugate reagents for treating patients having diseases associated with the growth of new blood vessels (neovascularization) such as cancer, rheumatoid arthritis, the exudative form of macular degeneration, and atherosclerosis. The target for immunoconjugates of the invention is the trans-membrane receptor tissue factor expressed by endothelial cells of the neovasculature. Tissue factor also is expressed by many types of tumor cells. Therefore, therapeutic methods of the invention are especially efficacious in immunotherapy against a broad range of solid tumors. The therapeutic reagent is an immunoconjugate composed of a targeting domain and an effector domain (FIG. 1). The targeting domain is a mutated form of factor VII that binds with high affinity and specificity to tissue factor, but does not initiate blood coagulation. The effector domain is the Fc region of an IgG1 immunoglobulin.

2. Background of the Invention

Pathologic angiogenesis, the induction of the growth of blood vessels from the vessels in surrounding tissue, is observed in a variety of diseases, typically triggered by the release of specific growth factors for vascular endothelial cells. Pathologic angiogenesis can result in neovascularization, enabling solid tumor growth and metastasis, causing visual malfunction in ocular disorders, promoting leukocyte extravasation in inflammatory disorders, and/or influencing the outcome of cardiovascular diseases such as atherosclerosis. Collectively, these are sometimes referred to as angiogenic diseases.

Since the survival and growth of a solid tumor depend critically on the development of a neovasculature, cancer is a paramount angiogenic disease (Folkman, J. (1995) *N. Engl. J. Med.* 333, 1757-1763). Many cancers progress in stages, beginning with proliferation of primary tumor cells, then penetration of tumor cells into the circulatory system, colonization at disseminated metastatic sites, and proliferation of the metastasized tumor cells which are responsible for most deaths from cancer (Vogelstein, B., and Kinzler, K. W. (1993) *TIG* 9, 141-143). Because cancer often remains undetected until the disease has reached the metastatic stage, cancer therapies that can eradicate the vascular infrastructure and metastatic tumor cells are particularly desirable.

Angiogenesis also plays a significant role in rheumatoid arthritis (Szekanez, Z., et al. (1998) *J. Invest. Med.* 46, 27-41). Rheumatoid arthritis (RA) is a chronic systemic inflammatory disease that occurs worldwide in all ethnic groups and predominantly affects diarthrodial joints and frequently a variety of other organs. The RA synovial tissue is extensively neovascularized. In RA, inflammatory leukocytes emigrate into the synovium through the endothelial layer of blood vessels, resulting in synovial inflammation and, eventually, joint destruction.

Angiogenesis underlies the majority of eye diseases that result in catastrophic loss of vision (Friedlander, M., et al. (1996) *Proc. Natl. Acad. Sci. USA* 93, 9764-9769). The leading cause of blindness in individuals over the age of 55 is the exudative ("wet") form of age-related macular degeneration (ARMD), and under the age of 55, proliferative diabetic retinopathy (PDR). While ARMD and PDR are prototypic diseases for choroidal and retinal neovascularization, respectively, other degenerative or inflammatory conditions can selectively cause angiogenesis of either vasculature (ibid.).

Therefore, one approach to the treatment of these disease states, and particularly of cancer, has been to compromise the function or growth of the neovasculature, primarily by inhibiting the growth of new blood vessels (Chaplin, D. J., and Dougherty, G. J., (1999) *Br. J. Cancer,* 80, 57-64). There are several advantages to vascular targeting. First, damage to blood vessels could stop blood flow and, applied to cancer, can trigger death of many dependent tumor cells. Second, the target cells are adjacent to the bloodstream, enhancing drug delivery. Third, treatment-resistant mutations are not likely to emerge in vascular endothelial cells.

A number of anti-angiogenic therapies have been suggested, including drug, antibody, and gene therapy-based approaches. These include metalloproteinase inhibitors, pentosan polysulphate and TNP-470, selective inhibitors of tyrosine kinase, and peptide inhibitors of angiostatin and endostatin (ibid., and reviews cited therein). These typically prevent angiogenesis at various stages of vessel formation, i.e., basement membrane degradation, endothelial cell migration, endothelial cell proliferation, and tube formation. It would be desirable to have improved therapies that target not only angiogenesis, but also the neovasculature already formed in angiogenic disease states.

SUMMARY OF THE INVENTION

It is an objective of the invention to provide a novel treatment for diseases involving the growth of new blood vessels (neovasculature), including cancer, rheumatoid arthritis, the exudative form of macular degeneration, and athlerosclerosis. It is another and more specific objective of the invention to provide a neovascular-targeted therapy that not only inhibits the angiogenesis observed in these disease states, but also destroys the neovasculature structure.

These and other objectives are accomplished by the present invention, which provides compositions comprising an immunoconjugate containing a targeting domain that binds selectively to tissue factor and an effector domain that mobilizes a cytolytic immune response or cytotoxic response against a targeted cell. In a typical immunotherapy treatment, a composition containing at least one immunoconjugate constructed as a dimer of two identical chains, each having an effector domain which is the Fc region of a human IgG1 immunoglobulin, including the hinge, conjugated to a targeting domain comprising a mutant form of human factor VII such as a factor VII with a substitution of alanine for lysine-341 and/or alanine for serine-344, that binds to tissue factor but does not initiate blood clotting, is administered in effective amounts to a patient having a disease associated with neovascularization. Since tissue factor is expressed by endothelial cells lining the tumor neovasculature but not the normal vasculature, and also by many types of tumor cells, factor VII immunoconjugates of the invention are especially efficacious in immunotherapy against a broad range of solid tumors. The invention is different from previously described inventions which activate coagulation in the neovasculature and/or introduce tissue factor or tissue factor mutants to the neovasculature (such as that described by Edgington and Morrissey in U.S. Pat. No. 6,001,978), which is superfluous because tissue factor is specifically expressed by the endothelial cells of the neovasculature, in two major respects: tissue factor is used as a target for inducing a cytolytic immune response mediated by immunoconjugates of the invention, rather than as an initiator of the blood coagulation process, and a cytolytic immune response that destroys neovasculature without activating the blood coagulation pathway is initiated.

Methods for systemic or local administration of the immunoconjugates are also disclosed, which involve the use of purified immunoconjugate proteins in conventional pharmaceutical compositions, or vector systems carrying a cDNA encoding a secreted form of the immunoconjugate. Treatments according to the invention include, but are not limited to, periodic or continuous intravenous or intratumoral injection, or injection at other sites, of effective amounts of one or more types of purified immunoconjugate protein. Alternate embodiments involve the treatment of patients by intravenous or intratumoral injection, or injection at other sites, of an effective amount of an expression vector carrying a cDNA encoding a secreted form of one or more types of immunoconjugate protein. Examples of the latter include treatment of patients by intravenous or intratumoral injection, or injection at other sites, of a replication-deficient adenoviral vector or an adeno-associated vector carrying a cDNA encoding a secreted form of immuno-conjugates of the invention.

In some embodiments such as cancer immunotherapy, immunoconjugates of the invention are administered together with another type of immunoconjugate having a different targeting domain. These typically are single-chain Fv or $V_H$ molecule fragments isolated from a human scFv or $V_H$ fusion phage libraries that bind selectively to cell surface molecules expressed on tumor cells, vascular endothelial cells, invasive cells in the synovium in pathological conditions, and the like.

BRIEF DESCRIPTION OF THE FIGURES

FIG. 6 is a line graph showing the inhibitory effect of the G71-1 and mfVIIasm immunoconjugates on the growth of a human melanoma xenograft in SCID mice. For each curve 5 SCID mice were injected subcutaneously with $5\times10^5$ TF2 cells. When the xenografts had grown to a palpable size, the mice received tail vein injections on days 0, 7 and 14 of the adenoviruses indicated in the figure. The amount of adenovirus injected was $4\times10^{11}$ for the control, $2\times10^{11}$ for the adenovirus encoding the G71-1 immunoconjugate and $4\times10^{11}$ for the adenovirus encoding the mfVIIasm immunoconjugate. The estimated tumor volumes are the averages for the 5 mice in each group.

the estimated tumor volumes on subsequent days are the averages for the remaining 4 mice.

Figure 9:
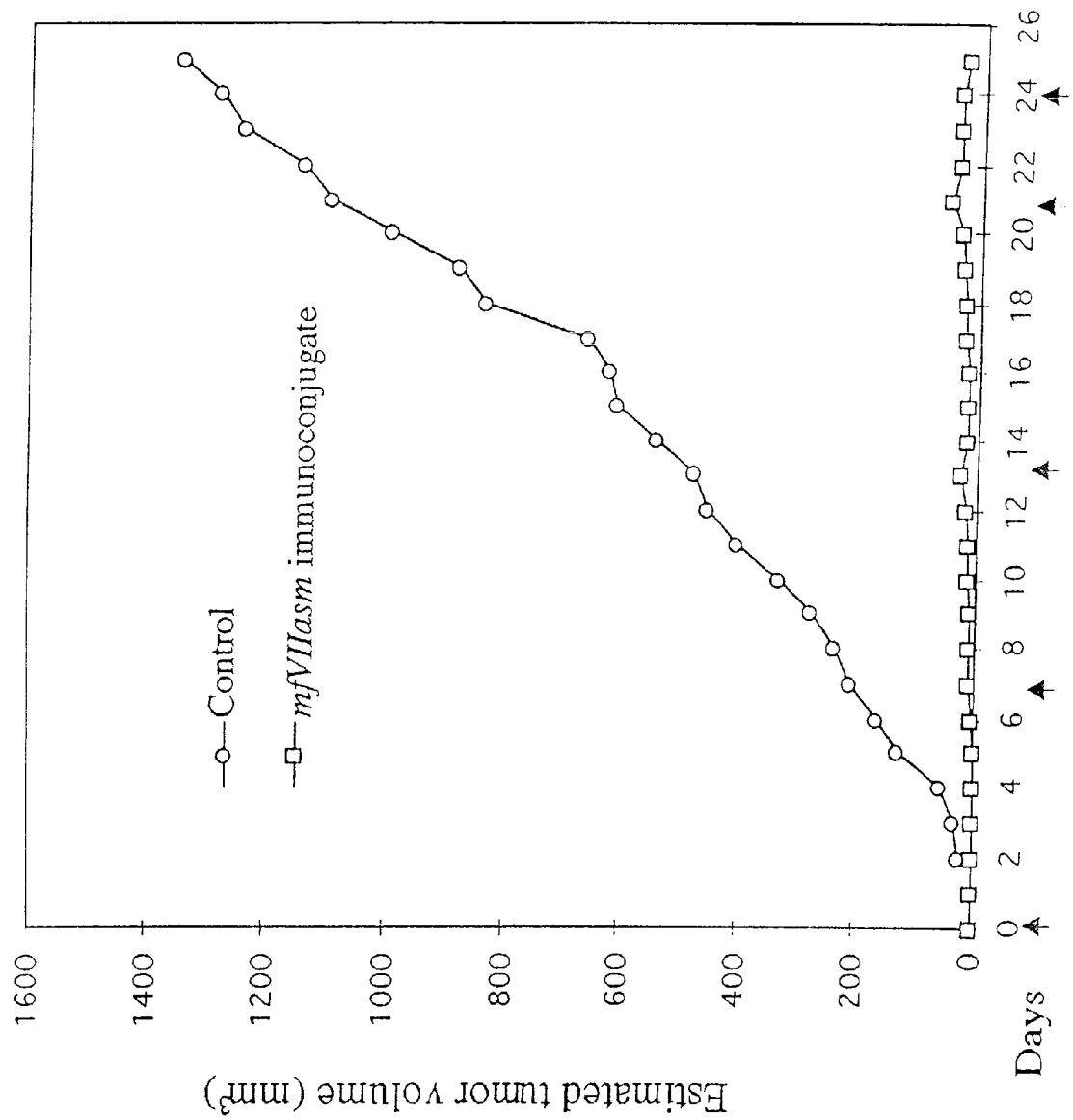

FIG. 9 is a line graph plotting the inhibitory effect of the mfVIIasm immunoconjugate on the growth of a human melanoma xenograft expressing a low level of tissue factor. The mice were injected subcutaneously with $5 \times 10^5$ LXSN cells, and when the xenograft had grown to a palpable size (day 0) 5 mice were injected intravenously with $9 \times 10^{11}$ adenoviruses encoding the mfVIIasm immunoconjugate, and 5 mice were injected with $4 \times 10^{11}$ control adenoviruses. Additional injections were done on days 7, 13, 21 and 24, and on day 25 the mice were dissected for morphological and histochemical examination. The estimated tumor volumes are the averages for the 5 mice in each group.

FIG. 10 illustrates the histochemistry of the human melanoma xenografts from the experiment reported in the legend of FIG. 9 and Example 2. The xenografts were dissected on day 25, embedded in paraffin, and sections were stained with hemotoxylin+eosin. Panel A: Xenograft from a control mouse injected with the adenovirus that does not encode an immunoconjugate. Panel B: Xenograft from a mouse injected with the adenovirus encoding the mfVIIasm immunoconjugate.

Figure 11:
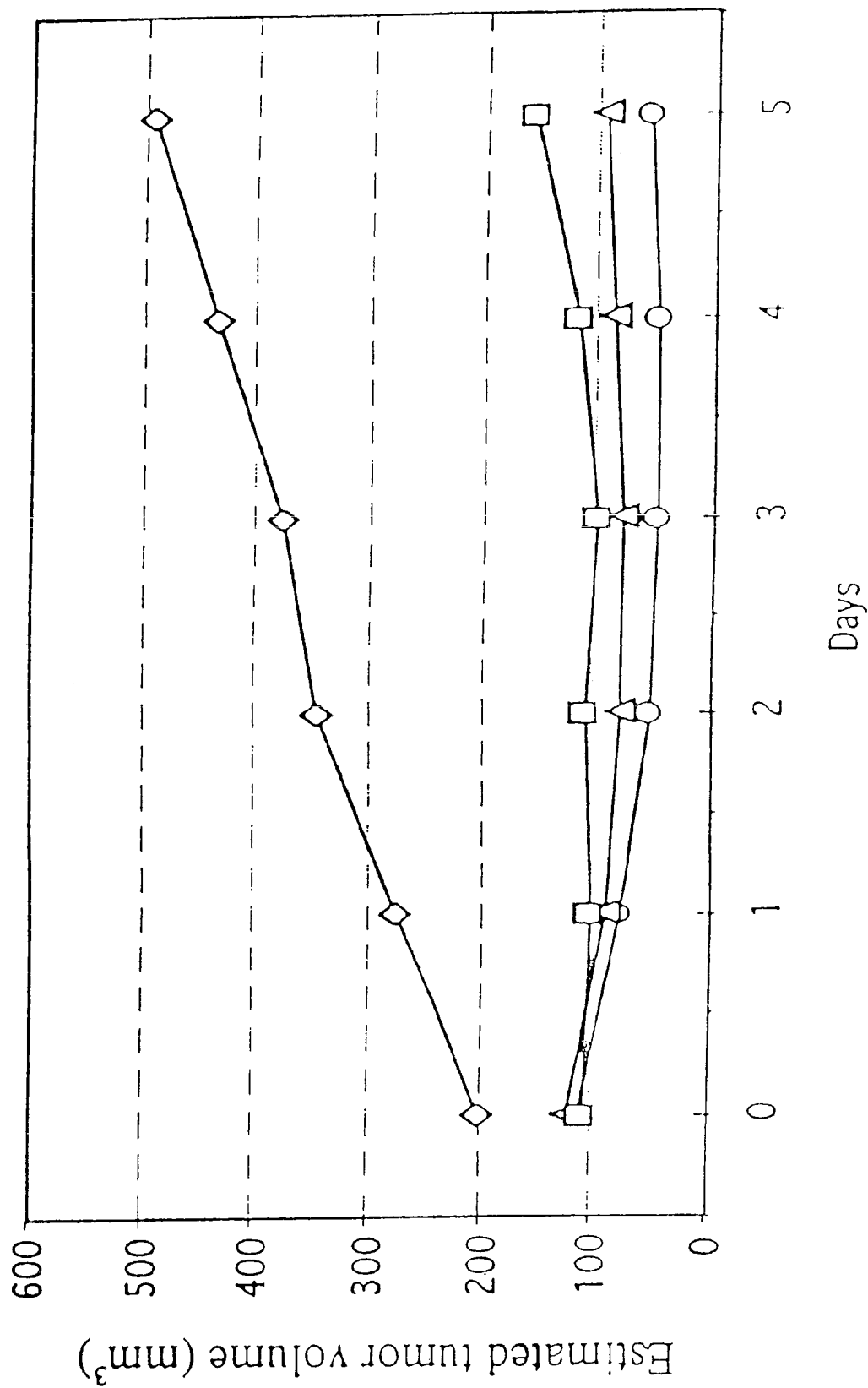

FIG. 11 is a line graph showing dosage effect of intratumorally injected adenoviral vectors on the growth of a human melanoma tumor in SCID mice. The mice were first injected subcutaneously with the human melanoma cell line TF2, and when a skin tumor had grown to the size indicated on day 0 the tumor was injected with a mixture of the two adenoviral vectors encoding the mfVIIasm and G71-1 immunoconjugates. The dose for the two vectors was as follows. ○: $7 \times 10^8$ IU; ∇: $2 \times 10^9$ IU; □: $6 \times 10^9$ IU. The dose for the control, ◇, was injected with $6 \times 10^9$ IU of an adenoviral vector that did not encode an immunoconjugate.

Figure 12:
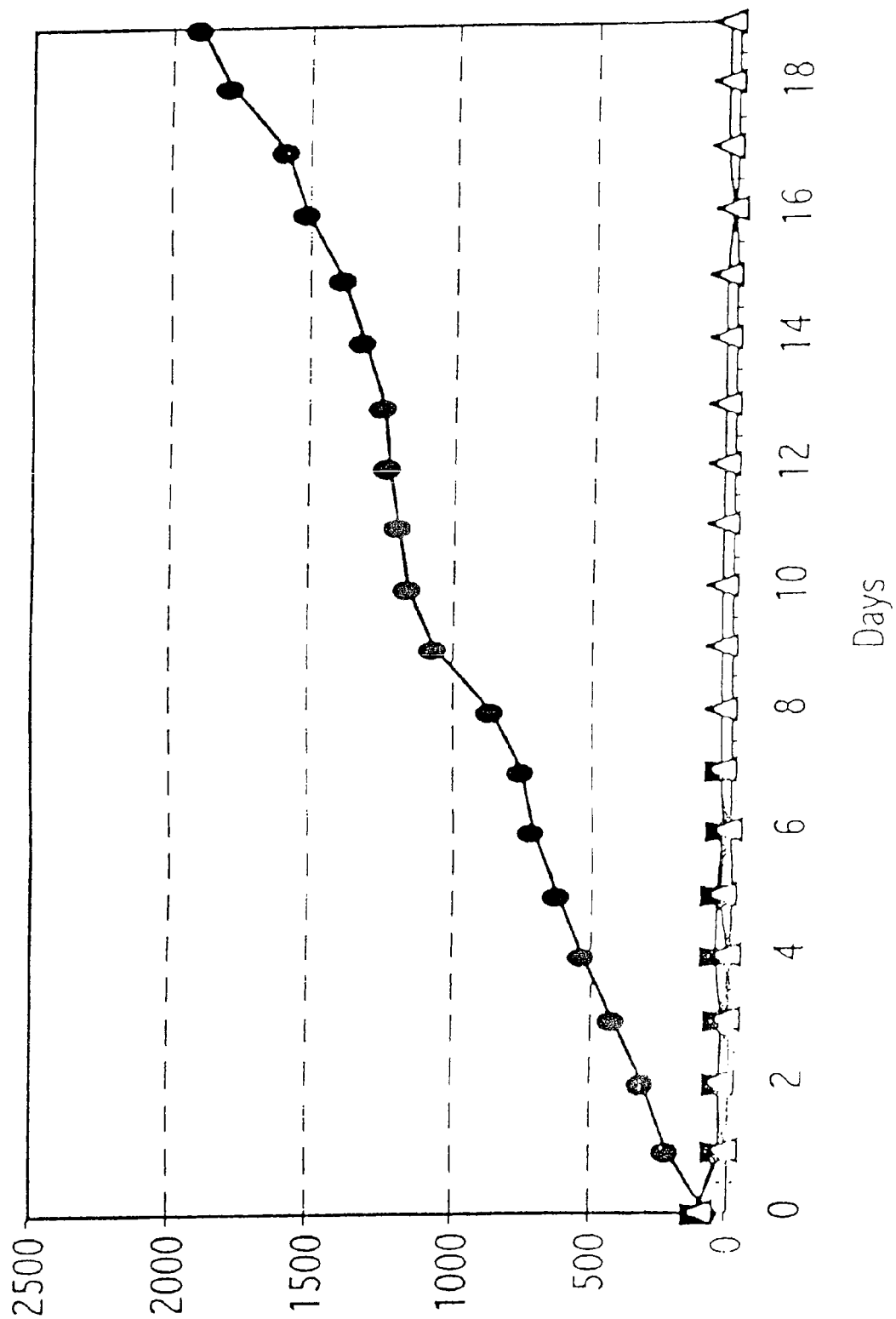

FIG. 12 is a line graph showing the effect of a high dose of intratumorally injected adenoviral vectors on the growth of a human melanoma tumor in SCID mice. The mice were first injected subcutaneously with the human melanoma line TF2, and when a skin tumor had grown to the size indicated on day 0 the tumor was injected with $6 \times 10^9$ IU of the following adenoviral vectors: ●, Control vector (3 mice); ■, vector encoding the mfVIIasm immunoconjugate (5 mice); >, mixture of the two vectors encoding the mfVIIasm and G71-1 immunoconjugates (6 mice). Additional injections were done on days 2, 5, 7, 9, 11, 13, 15 and 17. The points on each curve are the average ($\pm 20\%$) of the measurements for all mice in the corresponding group.

Figure 13:
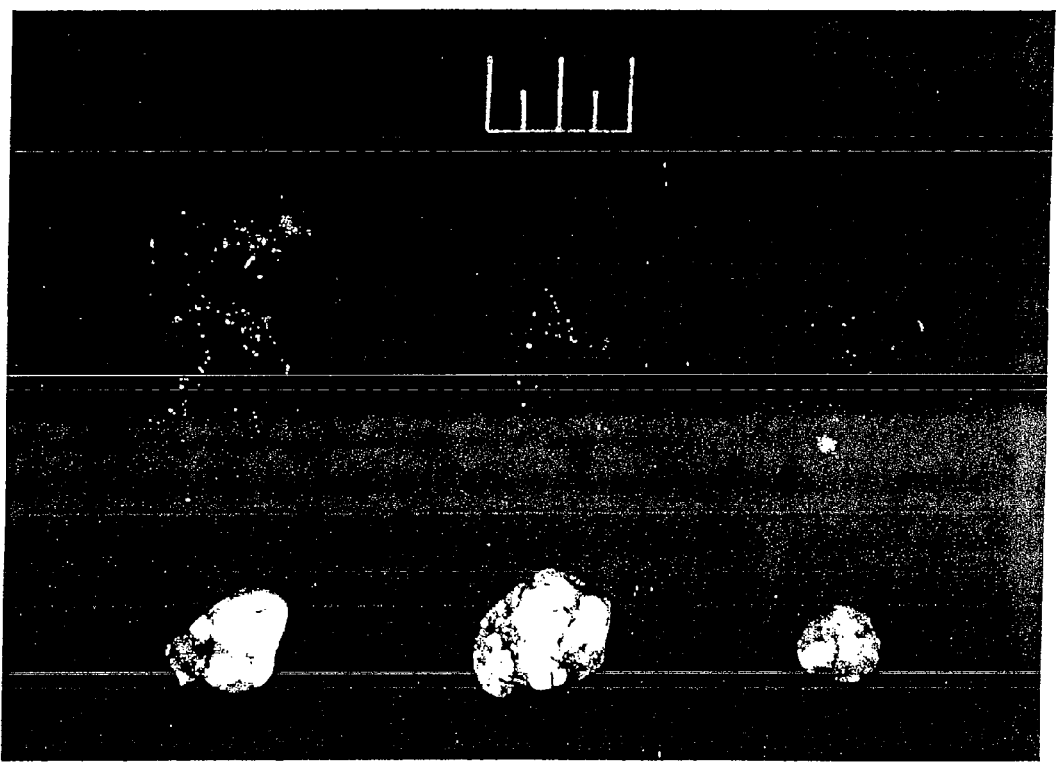

FIG. 13 are photographs of melanoma tumors from SCID mice injected intratumorally with the adenoviral vectors encoding a mixture of the mfVIIasm and G71-1 immunoconjugates or with an empty adenoviral vector control. The experiment is described in the legend to FIG. 12 above, and in Example 3. The tumors were dissected 2 days after the last injection and photographed. The full scale at the top of the figure is 1 cm.

Figure 14:
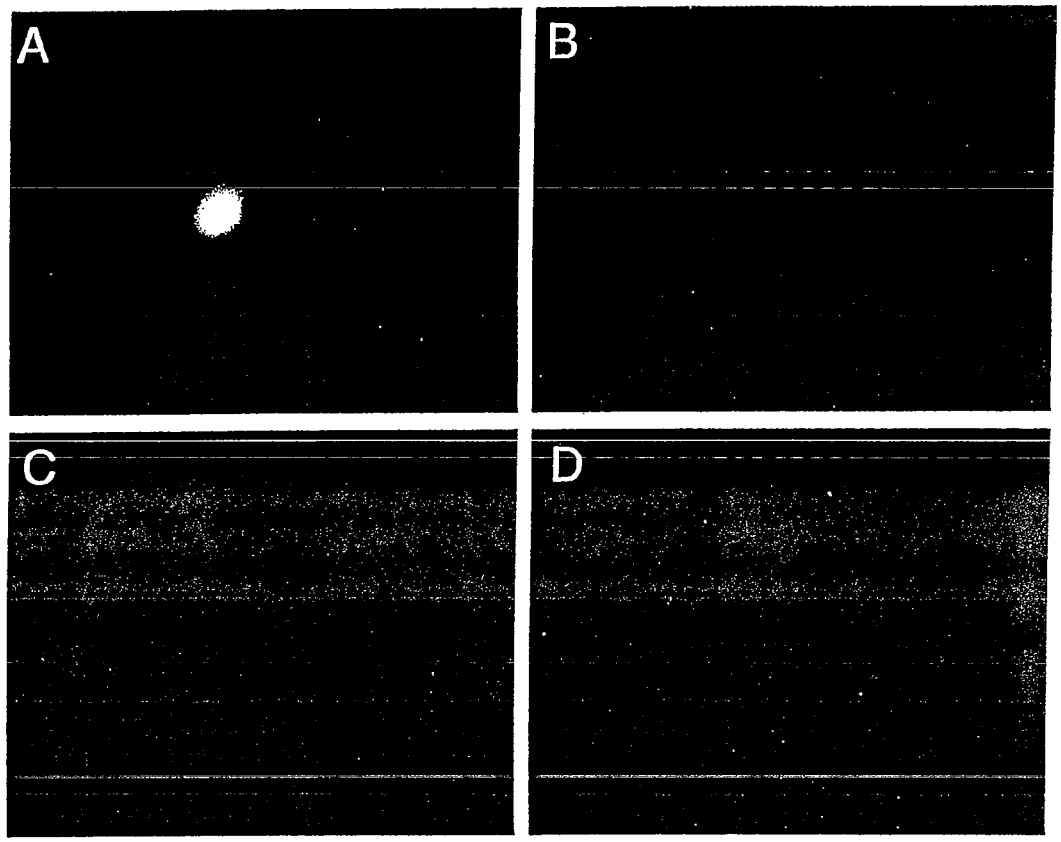

FIG. 14 are photographs showing the distribution of an adenoviral vector in tumor and liver after intratumoral injection. The control vector encoding the GFP protein but not an immunoconjugate was injected into 3 sites of a human melanoma skin tumor growing in SCID mice. The total vector dose was $6 \times 10^9$ IU. The tumor and liver were dissected 40 hr after the injection and were examined intact under a dissecting microscope with fluorescence optics. The GFP signal was detected with 480 nm excitation and 630 nm emmission, and the background signal was detected with 577 nm excitation and 630 nm emission. Panel A: Tumor GFP. Panel B: Tumor background. Panel C: Liver GFP. Panel D: Liver background.

A bright fluorescent spot similar to the one in Panel A also was detected at two other tumor sites, presumably corresponding to the injection sites. The photographs are focused at one level in the tissues. However, the GFP spot in the tumor also could be detected by focusing above and below that level, suggesting that the tumor cells adjacent to the path traversed by the injection needle are the only cells infected by the vector.

FIG. 15 shows liver sections from SCID mice injected intravenously or intratumorally with the adenoviral vectors. The intravenous experiment is described in Example 2, and the intratumoral experiment is described in Example 3. The panels on the left were injected with the control vector, and the panels on the right were injected with a mixture of the two vectors encoding the mfVIIasm and G71-1 immunoconjugates. The livers were dissected 2 days after the last injection, fixed in formaldehyde and embedded in paraffin. The sections were stained with hematoxylin and eosin and photographed at a magnification of 100×.

Figure 16:

FIG. 16 is a line graph showing the effect of intravenous injections into immunocompetent mice of the adenoviral vector encoding the mfVIIasm immunoconjugate on the growth of a mouse skin melanoma. C57BL/6 mice were injected subcutaneously with the mouse melanoma line B16F10, and when a skin tumor had grown to the size indicated on day 0 the tumor was injected with $3 \times 10^{10}$ IP of the vector encoding the mfVIIasm immunoconjugate. The Fc domain of the immunoconjugate was derived from a mouse IgG1 immunoglobulin. The tumor was injected again on day 5 with $1.5 \times 10^{10}$ IP.

DETAILED DESCRIPTION OF THE INVENTION

Anti-vasculature immunoconjugate therapy is based on the observation that normal adult mammalian vasculature is generally in a quiescent state (except for certain processes such as the female reproductive cycle and wound healing), in contrast to the neovasculature that forms in certain disease states such as a growing tumor which is in an active state of angiogenesis. Therefore, any molecular difference between quiescent and proliferating vascular endothelial cells could serve as a target for the pathologic vasculature.

A switch from a quiescent state to an angiogenic state in the pathologic vasculature such as that observed in cancer is usually activated by vascular endothelial growth factor (VEGF), which is secreted by tumor cells and binds with high affinity and specificity to VEGF receptors on vascular endothelial cells. Another response activated by the binding of VEGF to receptors on vascular endothelial cells is the expression of tissue factor, a transmembrane receptor that binds plasma factor VII/VIIa to initiate blood coagulation. Because only the vascular endothelial cells that have bound VEGF express tissue factor, a putative target for the tumor vasculature is tissue factor expressed on endothelial cells which should bind factor VII/VIIa circulating in the blood.

This invention is based upon the finding that immunoconjugates composed of a targeting domain conjugated to the Fc domain of human IgG1 mediate a cytolytic response against targeted cells by the natural killer (NK) cell and complement pathways of the immune system (Wang, B., et al. (1999) *Proc. Natl. Acad. Sci. USA* 96, 1627-1632). Since the binding between the cell surface receptor tissue factor expressed the inner surface of growing blood vessels, but not of the stable blood vessels present in normal tissues, and its natural ligand factor VII exhibits high specificity and affinity (Hu, Z., et al. (1999) *Proc. Natl. Acad. Sci. USA* 96, 8161-8166), the invention provides a new immunotherapy protocol for the treatment of diseases associated with neovascularization. The invention also provides enhanced efficacy for cancer treatments because tissue factor is also expressed by many types of tumor cells (Callander, N. S., et al. (1992) *Cancer,* 70, 1194-1201).

However, because the binding of a factor VII immunoconjugate to tissue factor might cause disseminated intravascular coagulation, factor VII mutants that inhibit coagulation without affecting affinity for tissue factor are employed in preferred embodiments of the invention. These immunoconjugates that bind to tissue factor but do not initiate blood clotting compete with endogenous factor VII/VIIa for binding to tissue factor. This competition strongly favors the immunoconjugate (Hu, et al., cited above) because it contains two factor VII targeting domains (FIG. 1), providing an avidity effect lacking in the monomeric endogenous factor VII molecule. In many preferred embodiments, the active site of human factor VII is mutated by site-directed mutagenesis, substituting alanine for Lys-341 and/or for Ser-344, in order to block the proteolytic activity that initiates the blood coagulation process when factor VII binds to tissue factor. Because both the targeting and effector domains can be derived from human sources, significant immune rejection responses in human patients are minimized.

Figure 1:
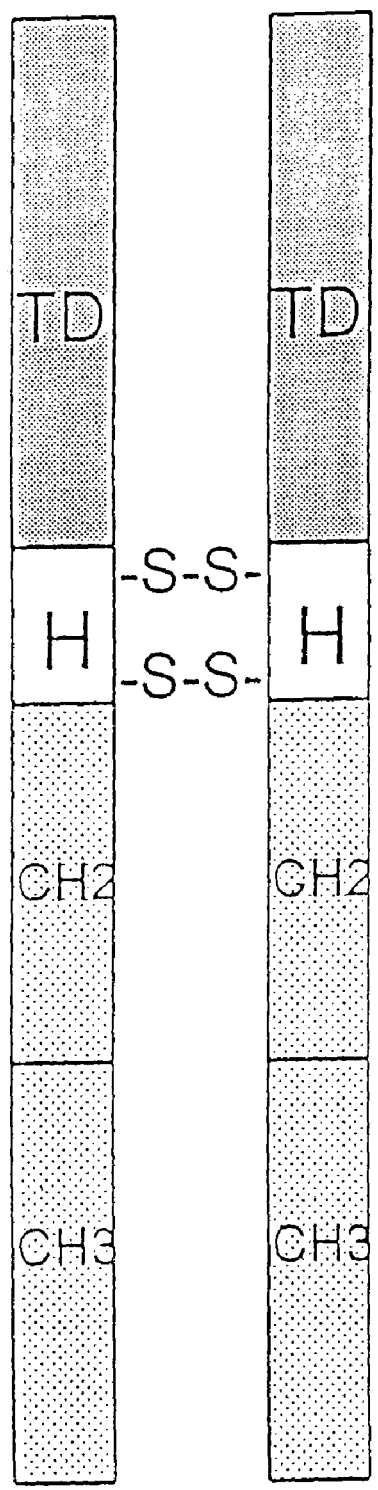
FIG. 1 is a diagram illustrating the organization of an immunoconjugate molecule of the invention. TD: Targeting domain. H: Hinge region of an IgG1 immunoglobulin with 2 disulfide bridges. CH2 and CH3: Constant regions of an IgG1 immunoglobulin. The targeting domain typically consists of human factor VII with a mutated active site or a human scFv or $V_H$ molecule. The effector domain typically consists of the Fc region of a human IgG1, unmodified or conjugated to a cytotoxic agent such as a radioactive molecule or photoactivatable dye molecule

In the generalized practice of the invention, immunoconjugates such as that set out in FIG. 1 are constructed as a protein dimer comprising two chains, each having an effector domain conjugated to a targeting domain. Several types of effector domain may be employed, so long as these exhibit cytotoxicity upon binding of the immunoconjugate to its target. Many typical immunoconjugate proteins of the invention have, as an effector domain, the Fc region of an IgG1 immunoglobulin. As used herein, this includes variants and truncated versions exhibiting the same biological function as the Fc region. In other embodiments, the effector domain can be a cytotoxic agent such as a radioactive tag or photoactivatable dye molecule, e.g., a dye that can be activated by a laser beam. The effector domain is conjugated to a targeting domain comprising a mutant form of factor VII that binds to tissue factor but does not initiate blood clotting as described above.

Immunoconjugate proteins of the invention are administered to a patient having a disease associated with neovascularization such as cancer, rheumatoid arthritis, the exudative ("wet") form of macular degeneration, or atherosclerosis. Administration may be local or systemic, depending upon the type of pathological condition involved in the therapy. As used herein, the term "patient" includes both humans or other species; the invention thus has both medical and veterinary applications. In veterinary compositions and treatments, immunoconjugates are constructed using targeting and effector domains derived from the corresponding species.

Administration can be via any method known in the art such as, for example, intravenous, intramuscular, intratumoral, subcutaneous, intrasynovial, intraocular, intraplaque, or intradermal injection of the purified immunoconjugate or of a replication-deficient adenoviral vector, or other viral vectors carrying a cDNA encoding a secreted form of the immunoconjugate. Other routes of administration can be parenteral administration of fluids, and the like. In preferred embodiments, the patient is treated by intravenous or intratumoral injection, or injection at other sites, of one or more immunoconjugate proteins, or by intravenous or intratumoral injection, or injection at other sites, of one or more expression vectors carrying a cDNA encoding a secreted form of one or more types of immunoconjugate proteins. In some embodiments, the patient is treated by intravenous or intratumoral injection of an effective amount of one or more replication-deficient adenoviral vectors, or one or more adeno-associated vectors carrying cDNA encoding a secreted form of one or more types of immunoconjugate proteins. A method employing a replication-deficient adenoviral vector is illustrated hereafter. Many typical embodiments involve intratumoral and/or intramuscular injections of effective amounts of a vector encoding a secreted form of an immunoconjugate. Where vectors are employed for cancer, intratumoral injection of the vectors provides an important safety advantage over intravenous injection, because the vector infects predominantly the cells of the injected tumor.

Administrations involving injections of immunoconjugate proteins employ compositions wherein the immunoconjugate protein, or a combination of proteins, is dispersed or solubilized in a pharmaceutically acceptable carrier. In some cases, immunoconjugates are synthesized in Drosophila S2 cells transfected with the expression vector pMK33/hygromycin, or in Chinese hamster ovary (CHO) cells transfected with the expression vector pcDNA3.1, or in a Baculovirus expression system, each vector carrying a cDNA encoding a secreted form of the immunoconjugate.

The amount of immunoconjugate necessary to bring about the therapeutic treatment is not fixed per se, and necessarily is dependent on the concentration of ingredients in the composition administered in conjunction with a pharmaceutical carrier, adjunct compounds in the composition administered that enhance the immune system response more fully illustrated below, and the age, weight, and clinical condition of the patient to be treated. Preferred compositions deliver immunoconjugate(s) in effective amounts without producing unacceptable toxicity to the patient. Pharmaceutical compositions or formulations of the invention may also include other carriers, adjuvants, stabilizers, preservatives, dispersing agents, and other agents conventional in the art having regard to the type of formulation in question.

As applied to cancer, the invention employs immunoconjugates having a targeting domain that specifically targets human tumor cells or tumor vasculature endothelial cells, or both, and an effector domain that activates a cytolytic immune response or cytotoxic effect against the targeted cells. As described above, immunoconjugates that have, as the effector domain, the Fc region of the IgG1 immunoglobulin, including the hinge, conjugated to mutant human factor VII that does not initiate blood clotting are particularly efficacious in many cancer treatments because they target tissue factor expressed both on tumor vasculature and tumor cells. In some embodiments, therapeutic effects can be further enhanced by administering to the patient another class of immunoconjugates that selectively target the tumor, such as immunoconjugates that have, as the targeting domain, an anti-human tumor cell scFv or $V_H$ antibody fragment isolated by panning a scFv or $V_H$ fusion-phage library, derived from the peripheral blood lymphocytes of cancer patients, against the tumor cells previously described (Cai, X., and Garen, A. (1997) *Proc. Natl. Acad. Sci. USA* 94, 9261-9266). Combinations of immunoconjugates, administered simultaneously or sequentially as described above, are particularly advantageous where synergy that enhances cytolysis of the targeted cells is observed.

In cancer treatments, anti-tumor immunoconjugates are used for treating a variety of cancers, particularly primary or metastatic solid tumors, including melanoma, renal, prostate, breast, ovarian, brain, neuroblastoma, head and neck, pancreatic, bladder, and lung cancer. The immunoconjugates may be employed to target the tumor vasculature, particularly vascular endothelial cells, and/or tumor cells. The tumor vasculature offers several advantages for immunotherapy, as follows. (i) Some of the vascular targets including tissue factor should be the same for all tumors. (ii) Immunoconjugates targeted to the vasculature do not have to infiltrate a tumor mass in order to reach their targets. (iii) Targeting the tumor vasculature should generate an amplified therapeutic response, because each blood vessel nourishes numerous tumor cells whose viability is dependent on the functional integrity of the vessel. (iv) The vasculature is unlikely to develop resistance to an immunoconjugate, because that would require modification of the entire endothelium layer lining a vessel. Unlike previously described antiangiogenic methods that inhibit new vascular growth, immunoconjugates of the invention elicit a cytolytic response to the neovasculature.

Immunoconjugates of the invention can also be effective for treating patients with rheumatoid arthritis, the exudative ("wet") form of macular degeneration, atherosclerosis, and other diseases associated with neovascularization. Administering an immunoconjugate targeted to tissue factor by a mutated human factor VII, which is conjugated to the Fc domain of an IgG1 immunoglobulin, can generate a cytolytic immune response against the vascular endothelial cells that invade the synovium in rheumatoid arthritis and express tissue factor. Likewise, factor VII immunoconjugates can also be effective for treating the exudative (wet) form of macular degeneration because of the extensive neovascularization observed in that pathologic condition. Immunoconjugates of the invention can also be effective for the treatment of atherosclerosis by generating a cytolytic immune response against cells expressing tissue factor in plaques.

In summary, an overall immunotherapy program according to the invention involves constructing immunoconjugates containing, as the targeting domain, factor VII with a mutated active site, which binds with high avidity and specificity to tissue factor expressed on neovascular endothelial cells and also on tumor cells without causing blood coagulation. Immunoconjugates that contain as the effector domain the Fc region of an IgG1 immunoglobulin mediate the lysis of targeted cells by NK cells and complement, resulting in destruction of the neovasculature. A significant advantage of the invention is the fact that immunoconjugates containing two factor VII targeting domains, in contrast to endogenous factor VII monomeric molecules, exhibit significantly greater binding than exogenous factor VII to cells expressing tissue factor, successfully competing in the presence of excess natural ligand. Example 2 below illustrates an immunoconjugate that successfully competed in the presence of at least about a ten-fold molar excess of natural ligand, but the invention encompasses other embodiments exhibiting lower or higher affinity. The binding between endogenous factor VII to tissue factor is one of the most specific and strongest reactions known, with a $K_d$ in the picomolar range. Nevertheless, this invention improves significantly on the normal binding of factor VII to tissue factor as a result of the avidity effect of having two factor VII sequences in one immunoconjugate molecule. This avidity effect enhances the targeting and binding of immunoconjugates of the invention, so that they compete effectively with endogenous factor VII and the binding persists longer, so that the immune response elicited is maximized. The immune response may be further maximized by administering to a patient, as adjunct therapy, another immunoconjugate having an effector domain which is the Fc region of an IgG1 immunoglobulin conjugated to a targeting domain which is a scFv or $V_H$ antibody fragment that binds to neovasculature, and/or, in the case of cancer, to the patient's type of tumor cell.

EXAMPLES

The examples presented herein further illustrate and explain the present invention and should not be taken as limiting in any regard. Some of the methods used to generate and characterize immunoconjugates of the invention and component monoclonal antibodies have been described in Cai, X., and Garen, A. (1995) Proc Natl. Acad. Sci. USA 92, 6537-6541, (1996) Proc. Natl. Acad. Sci. USA 93, 6280-6285, and the 1997 reference cited above; in PCT/IB96/01032 to Yale University and Garen and Cai, published 23 Jan. 1997 as WO 97/02479, in the U.S. application Ser. No. 08/983,607 filed Apr. 27, 1998, allowed Mar. 3, 2000; in Wang, et al., cited above; and in Hu, Z., et al., cited above.

Example 1

Immunoconjugates containing a human single-chain Fv (scFv) targeting domain conjugated to the Fc effector domain of human IgG1 are synthesized and tested in this example. The scFv targeting domains were originally isolated as melanoma-specific clones from a scFv fusion-phage library, derived from the anti-body repertoire of a vaccinated melanoma patient (more fully described in the Cai and Garen references cited above). The purified immunoconjugates showed similar binding specificity as did the fusion-phage clones: Binding occurred to human melanoma cells but not to human melanocytes or to several other types of normal cells and tumor cells.

Materials and Methods. Cell cultures. The permanent human melanoma lines A2058 (American Type Culture Collection, Rockville, Md.) and TF2 were grown in DMEM+ 10% FCS. Primary cultures of human microvascular endothelial cells and fibroblast cells were extruded from newborn foreskin and cultured in RPMI medium supplemented with 8% FBS and 2% human peripartum serum; the endothelial cells were further supplemented with 33 mM 3-iso-butyl-1-methylxanthene (IBMX) and 0.5 mM dibutyryl cAMP. Primary cultures of human melanocytes from newborn foreskin were prepared by the Skin Disease Research Center at Yale University School of Medicine. The transformed human kidney cells 293-EBNA (Invitrogen) and the Chinese hamster ovary (CHO) cells were grown in RPMI+10% FCS. (v) Drosophila cells (Schneider S2) were grown at 25° C. in Ex-cell 301 medium (JRH biosciences)+10% FBS. Resting NK cells were isolated from normal donors by leukophoresis and immunoselection and were used within 18 hr after isolation; most of the cells (>97%) were CD3−, CD56+ and CD16+.

Preparation of the immunoconjugates. The procedures involved transfecting the expression vector pcDNA3.1 (Invitrogen) into CHO cells, or the expression vector pMK33/pMtHy into Drosophila cells; each vector carried a cDNA encoding a secreted immunoconjugate (FIG. 1). The cDNAs for the scFv targeting domains were synthesized from the corresponding fusion-phage (1) using PCR primers containing Sad or BamHI sites as, follows: a) GTCGAGCA-GAGCTCCAGGTGCAGCTGGTG-CAGTCTGGGGCTGAGGTGAGGTGAAGAAGCC (SEQ ID NO: 1); b) ACGTTCAGGGGATCCACCTAGGACGGT-CAGCTTGGTCCC (SEQ ID NO: 2). The human Fc effector domain was synthesized from a cDNA library derived from human peripheral blood lymphocytes, using PCR with primers containing BamHI and SalI sites, as follows: a) ACCT-TGCAGGATCCGCAAGACCCAAATCTTGT-GACAAAACTCAC (SEQ ID N: 3); b) GATCACGTGTCGACTTATCATTTACCCGGAG ACAGGGAGAGGCTCTTCTG (SEQ ID NO: 4). The cDNA for the IgG1 leader was synthesized by hybridizing two complementary oligonucleotides containing EcoRI and SacI ends, as follows: a) AATTCATGGAGTTTGGGCT-GAGCTGGCTTTTTCTTGTTGCTGCAT-TAAGAGGTGTCCAGTCCGAGCT (SEQ ID NO: 5); b) CGGACTGGACACCTGTTA ATGCAGCAACAA-GAAAAGCCAGCTCAGCCCAAACTCATG (SEQ ID NO: 6).

These three cDNAs encoding a secreted immunoconjugate were ligated first into a cloning vector for sequencing and then into the expression vectors pcDNA3.1 and pMK33/pMtHy for transfection into CHO or Drosophila S2 cells, respectively. The transfection procedure for CHO cells involved growing the cells in RPMI+10% FCS and transfecting with 5 µg of an expression vector using Superfect™ (Qiagen). Stable transfectants were selected in RPMI+10% FCS+1 mg/ml G418. For protein expression, transfected CHO cells were first adapted to growth in CHO serum-free medium (Sigma), and then were grown for 3 days as a suspension culture ($2\times10^5$ cells/ml) in the serum-free medium. The transfection procedure for Drosophila S2 cells involved growing the cells in Ex-cell medium+10% FBS and transfecting with 10 µg of an expression vector using Lipofectin™ (Gibco-BRL). Stable transfectants were selected in Ex-cell medium+10% FBS+300 µg/ml hygromycin, and adapted for growth as a suspension culture in serum-free Ex-cell medium. Expression of the encoded immunoconjugate was induced in the suspension culture by addition of 500 µM copper sulfate.

The immunoconjugates secreted by transfected CHO or Drosophila S2 cells were purified from the culture medium by affinity chromatography on a protein-A matrix (Pierce).

Binding specificity of the immunoconjugates measured by fluorescence-activated cell sorting (FACS). Melanoma cells and control cells were harvested in non-enzymatic dissociation medium (Sigma), washed with PBS/BSA+0.1% sodium azide, and incubated in PBS/BSA with added immunoconjugate (1 µg/ml) or in PBS/BSA without an immunoconjugate as a control. The cells were washed with PBS/BSA, incubated 30 mM at 4° C. with fluoroscein-labeled anti-human Fc γ-chain (Vector), and analyzed on a Becton-Dickenson FACsort instrument.

Immunoprecipitation of a melanoma cell extract with an immunoconjugate. A sample of about $1\times10^7$ cells from the human melanoma line A2058 was suspended in a solution containing 10 µg/ml immunoconjugate, 1% BSA and 0.05% sodium azide in PBS, and was incubated for 30 minutes on ice. The cells were washed twice with PBS and lysed in a solution containing 1% NP-40, 1 µg/ml immunoconjugate and 0.2 mM PMSF in PBS for 20 minutes on ice. The lysate was spun at 13,000 RPM in microfuge for 5 mM, and the supernate was recovered and incubated with protein-G beads overnight on a rotator. The beads were collected, washed twice with a solution containing 1% NP-40 in PBS and once with PBS, and the beads were collected, boiled in PAGE loading buffer and analyzed by PAGE.

Matrix-Assisted Laser Desorption Ionization-Mass Spectrometry (MALDI-MS) and Liquid Chromatography Tandem MS (LC/MS/MS) protein identification. A protein band stained with Coomassie Blue was excised from the gel and digested with trypsin A sample of the tryptic digest was analyzed by MALDI-MS on a Micromass TofSpec SE. To attain the high level of accuracy needed for peptide mass searching, 100 fmol bradykinin which has a protonated monoisotpic mass of 1060.57, and ACTH clip which has a protonated monoisotopic mass of 2465.2, were used as internal calibrants. The resulting monoisotopic masses of the tryptic peptides were searched against the OWL database with the ProFound program using a mass tolerance of 0.2 daltons, and against the EMBL/non-redundant database with the PeptideSearch program using a 0.015% mass tolerance. Other important criteria used in the search were a mass range that extended from 140-560 Kda, a maximum of 1 missed cleavage and no limitation with regard to taxonomy. All the protein chemistry and mass spectronomy studies were carried out in the W. M. Keck Foundation & HHMI Biopolymer Laboratory at Yale University.

A sample of the trypsin-digested protein band used for the MALDI-MS analysis was also analyzed on a LCQ ion trap mass spectrometer. A Sequest search of the MS/MS data was done, using a tandem mass correlation algorithm with a mass tolerance of 2.0 daltons, to determine whether significant similarities exist between peptides from the tryptic digest and the reconstructed theoretical spectra for a protein in the NCBI or database. Further information about this procedure can be obtained at Assays for immunoconjugate-dependent cytolysis of human melanoma cells by NK cells and complement. The Calcein-AM retention procedure was used for both assays. The target cells, either human melanoma lines or primary human fibroblast cells, were isolated from culture flasks in a non-enzymatic dissociation medium (Sigma) and added to 96-well plates ($2\times10^4$ cells/well). The adherent target cells were washed once with PBS, and afterwards incubated for 20 minutes at 37° C. in serum-free culture medium (GIBCO-BRL) containing an immunoconjugate (1 µg/ml) or without an immunoconjugate as a control. The target cells were then labeled with 7 µM Calcein-AM (Molecular Probes Inc., Eugene, Oreg.) in serum-free medium for 40 min at 37° C. Calcein-AM is a fluorescent dye that enters the cells, where it is enzymatically altered and remains intracellular until the cells are lysed. For the cytolytic assays involving NK cells, the labeled target cells were incubated 3-4 hr at 37° C. with human NK cells using the indicated ratios of NK cells to target cells. For the cytolytic assays involving complement, the labeled target cells were incubated 1 hr at 37° C. with human serum or purified rabbit complement components (Cedarlane Laboratories, Ontario, Canada). After incubation with NK cells or complement, the target cells were washed twice with PBS, and the fluorescence in the remaining adherent cells (residual fluorescence) was measured with a plate reader. The maximum attainable cytolysis of the target cells was determined by measuring residual fluorescence of the target cells after treatment with lysis buffer (50 mM sodium borate, 0.1% Triton X-100, pH 9.0) for 3 hr at 37'C. The maximum residual fluorescence was determined by measuring the fluorescence of adherent target cells that were not exposed to NK cells or complement. The % cytolysis for each sample of target cells was calculated as follows: (residual fluorescence of the sample target cells minus residual fluorescence of the lysed target cells)/(maximum residual fluorescence of the target cells minus residual fluorescence of the lysed target cells).

Results. Synthesis and characterization of the anti-melanoma immunoconjugates. The immunoconjugate encoded a human IgG1 leader for secretion, a human scFv domain for targeting melanoma cells, and a human IgG1-Fc effector domain (FIG. 1). The immunoconjugate molecules were expressed in transfected CHO and Drosophila S2 cells, and were purified from the culture medium as two-chain molecules linked by disulfide bridges in the hinge region of the Fc domain (FIG. 1). Two immunoconjugates were synthesized, each containing a scFv targeting domain derived from the fusion-phage clone E26-1 or G71-1. The binding specificities of the immunoconjugates E26-1 and G71-1 were tested by cell sorting (FACS) using two human melanoma lines; the controls were primary cultures of normal human melanocyte, fibroblast, microvascular and umbilical vascular endothelial cells, and the human kidney line 293-EBNA. The results showed that the immunoconjugates bind strongly to the melanoma cell lines but do not bind to the controls, consistent with the results obtained with the E26-1 and G71-1 fusion-phage clones. The binding to melanoma cells occurred when the cells were collected from the culture flask using a non-enzymatic cell dissociation medium (Sigma), but not when the dissociation medium contained trypsin or when the dissociated cells were subsequently treated with trypsin. This finding indicated that the cognate melanoma antigen(s) for the immunoconjugates is located on the surface of melanoma cells. The antigen(s) appear to be exceptionally sensitive to trypsin, since the same exposure to trypsin did not affect the binding to the melanoma cells of antibodies against the cell surface molecules ICAM-1, MHC class-1 and tissue factor.

Identification of the cognate melanoma antigen for the immunoconjugates. Cultured cells from the human melanoma line A2058 were equilibrated with the immunoconjugates G71-1 or E26-1, and the cells were lysed with detergent. The immunoconjugate-antigen complex in the lysate was collected on protein-G beads and analyzed by PAGE. A protein band with an apparent molecular weight of 250 kda was detected in the melanoma cells but not in the control. Analysis of a tryptic digest of the protein band by the MALDI-MS procedure identified 75 peptide masses that were not present in a digest of a control gel slice. A search of protein sequence databases by ProFound yielded 50 peptide masses that matched peptide masses in the MCSP core protein, spanning 26% of the complete protein sequence. The ProFound probability score for this identification was 1.0, and the next closest score was 2.2E-61. A search by Peptide Search matched 45 peptides to the MCSP core protein, with 38 peptides representing the next closest match.

The tryptic digest of the 250 kda protein was also analyzed by the LC/MS/MS procedure (Stone, K. L., et al. (1998) Electrophoresis 19, 1046-1052). A Sequest search of the MS/MS data from the tryptic digest showed significant similarity between the MS/MS spectra for two or more peptides and the reconstructed theoretical MS/MS spectra for two or more peptides from the MCSP core protein in the NCBI nr database.

The results of both mass spectroscopy analyses indicate that the melanoma protein immunoprecipitated by the immunoconjugates G71-1 and E26-1 matched the MCSP core protein.

Figure 2:
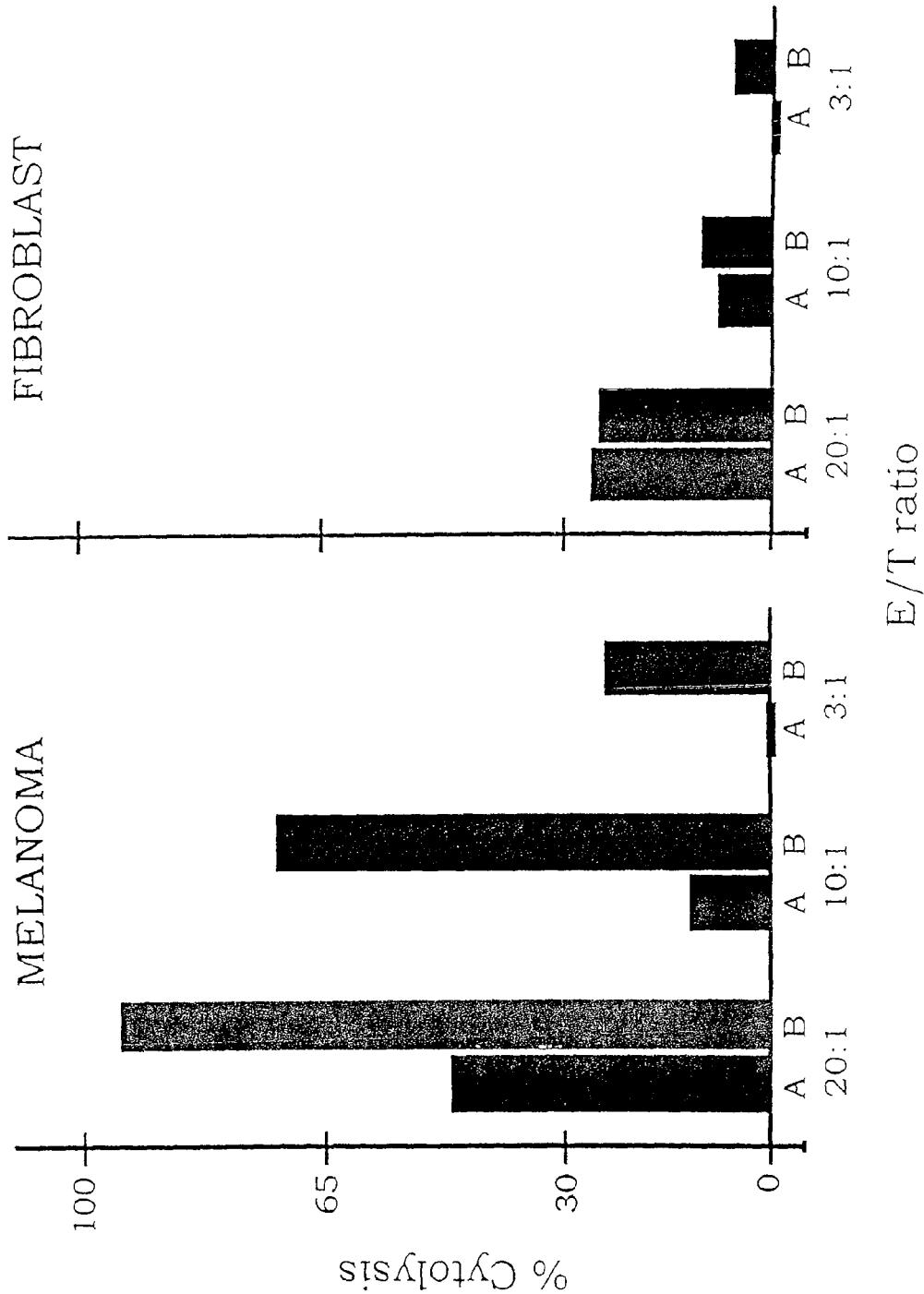
FIG. 2 is a bar graph showing immunoconjugate-dependent lysis of human melanoma cells by human natural killer (NK) cells. The targeting domain of the immunoconjugate is a melanoma-specific human scFv molecule, and the effector domain is the Fc region of a human IgG1 immunoglobulin. The human melanoma cell line A-2058 and the human fibroblast cell control were labeled with the fluorescent dye Calcein-AM. The fraction of melanoma or fibroblast cells remaining intact after exposure to NK cells alone (Bar A), or to NK cells with the scFv immunoconjugate E26-1 (Bar B), was measured by residual fluorescence. The ratio of NK effector cells to target cells (E/T) was varied from 3 to 20. Three complete sets of experiments were done for both the melanoma and fibroblast cells; for each experiment, the cytolysis assays were done in quadruplicate. The bars shown in the figure represent the average of the cytolysis assays for the three experiments, which generally agreed within 10%. The % cytolysis was calculated as described in Example 1. Similar results were obtained with the scFv immunoconjugate G71-1.

Immunoconjugate-dependent cytolysis of melanoma cells mediated by NK cells and complement. One of the cytolytic pathways of the immune system involves NK cells which can bind directly to target cells, causing antibody-independent lysis of the target cells. NK cells also bind to the Fc effector domain of an antibody, resulting in anti-body-dependent lysis of cells that bind to the targeting domain of the antibody. This antibody-dependent cell-mediated cytolytic pathway (ADCC) should also cause lysis of cells that bind to the targeting domain of immunoconjugates containing an Fc effector domain. To test for an ADCC response dependent on the immunoconjugates E26-1 and G71-1, melanoma cells and fibroblast control cells were labeled with the fluorescent dye Calcein-AM, and the labeled cells were incubated with human NK cells alone or together with an immunoconjugate. Cytolysis was assayed by measuring the amount of fluorescent dye retained in the cells that remained intact. The results for E26-1 (FIG. 2) show that after incubation with the immunoconjugate and NK cells, the percentage of lysed melanoma cells increased above the basal level that occurs without the immunoconjugate, reaching almost 100% lysis at a 20/1 ratio of NK cells to melanoma cells. In contrast to the efficient lysis of melanoma cells, the fibroblast cells showed no significant increase in cell lysis after incubation with the immunoconjugate and NK cells. Similar results were obtained with the G71-1 immunoconjugate.

The sensitivity of target cells to lysis by NK cells is increased by expression on the target cell surface of adhesion molecules such as ICAMs, and is reduced by expression of MHC class 1 molecules (Zami, L., et al. (1995) Cell. Immunol. 164, 100-104 and Storkus, W. J., et al. (1989) Proc. Natl. Acad. Sci. USA 86, 2361-2364). To determine whether differences in expression of these molecules might contribute to the differences in the sensitivities of melanoma cells and fibroblast cells in the ADCC assays, the expression of ICAM-1 and MHC class I molecules by melanoma and fibroblast cells was measured by FACS. Expression of both molecules was similar in the two cell types, indicating that the specific lysis of melanoma cells by NK cells depends on the binding of the immunoconjugates to the cognate antigens expressed on melanoma cells. Another cytolytic pathway of the immune system involves the complement cascade, which is activated when the molecule C1q reacts with the Fc region of antibodies bound to a target cell (Bruggemann M., et al. (1987) J. Exp. Med. 166, 1351-1361). To test for a complement-mediated cytolytic response against melanoma cells, dependent on the immunoconjugates E26-1 and G71-1, the same assay procedure employed for the NK-mediated cytolytic response reported above was used with one change, namely that human serum or rabbit serum, which contain the components of the complement cascade, was substituted for NK cells. The results (FIG. 3 and Table 1) show that after incubation with the immunoconjugates and either human serum or rabbit serum, there was an increase in the fraction of melanoma cells lysed from 4% to almost 100%. In contrast to the efficient lysis of melanoma cells, the fibroblast cells showed a small increase in the fraction of lysed cells after incubation with the immunoconjugates and human serum, and no significant increase after incubation with the immunoconjugates and rabbit serum.

TABLE 1

Figure 3:
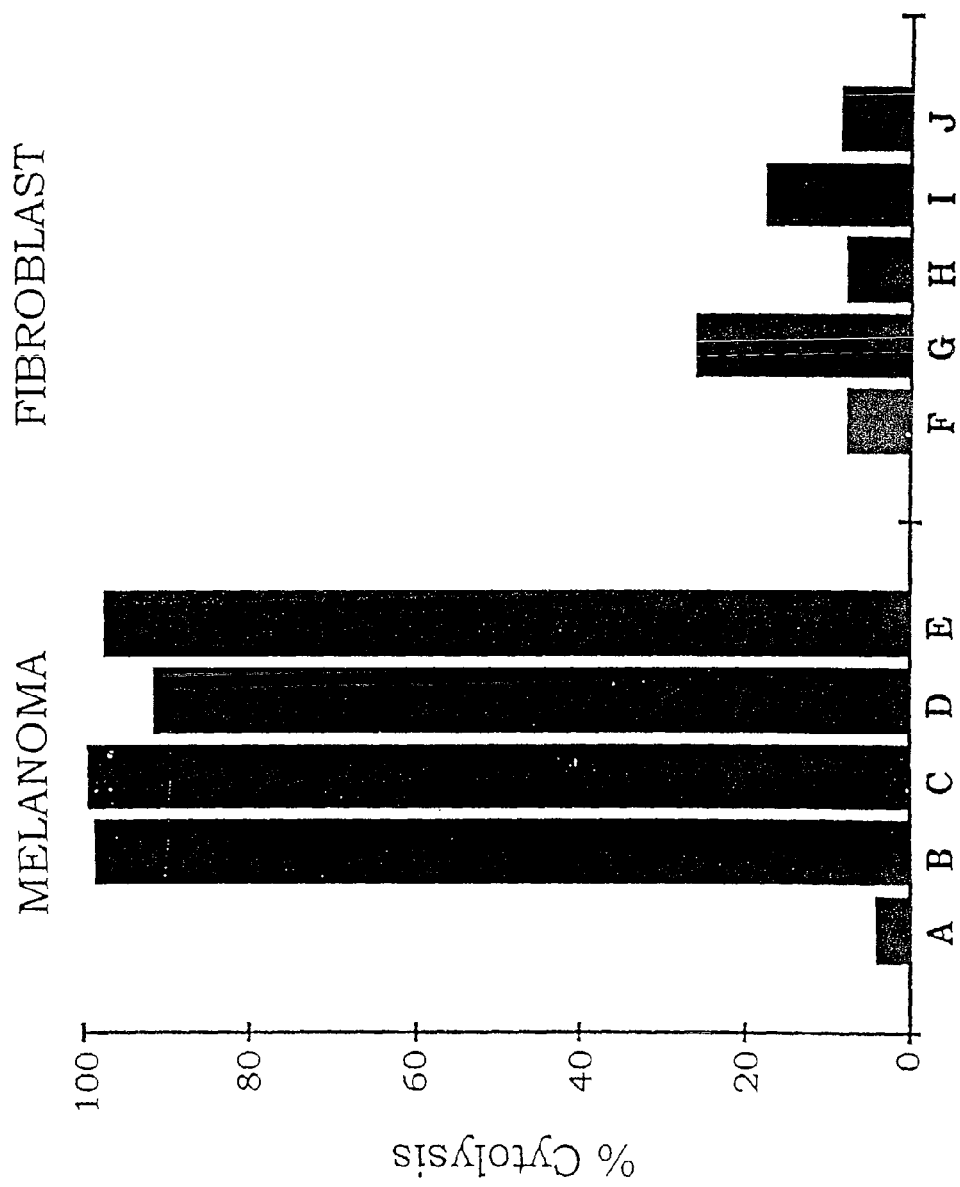
FIG. 3 is a bar graph showing immunoconjugate-dependent lysis of human melanoma cells by complement. The procedure was as described in the legend of FIG. 2, except that human serum or purified rabbit complement components were used instead of NK cells. Immunoconjugate and complement reagents for each assay were as shown in Example 1, Table 1.

Immunoconjugate and complement reagents used for FIG. 3 assays.

| Assay | Human serum | Rabbit complement | Immunoconjugate G71-1 | E26-1 |
|---|---|---|---|---|
| A, F | − | + | − | − |
| B, G | + | − | + | − |
| C, H | − | + | + | − |
| D, I | + | − | − | + |
| E, J | − | + | − | + |

Discussion. For the present study the scFv molecules from two of the clones were used as the targeting domains for constructing immunoconjugates containing a human IgG1-Fc effector domain (FIG. 1). The protein immunoprecipitated from human melanoma cells by both immunoconjugates was identified by mass spectroscopic analyses as the core protein of a melanoma-associated chondroitin sulfate proteoglycan (MCSP) (Bumol, T. F. & Reisfeld, R. A. (1982) Proc. Natl.

*Acad. Sci. USA* 79, 1245-1249 and Bumol, T., et al. (1984) *J. Biol. Chem.* 259, 12733-12741). The MCSP molecule was first identified as the cognate antigen recognized by the mAb 9.2.27, and it appears to be the cognate antigen for several other mAbs (Reisfeld, R. A. & Cheresh, D. A. (1987) *Adv. Immunol.* 40, 323-377; Wilson, B. S., et al. (1981) *Int. J. Cancer* 28, 293-300; Hellstrøm, I., et al. (1983) *J. Immunol.* 130, 1467-1472). Several scFv fusion-phage clones that bind to the melanoma antigen HMW-MAA, which probably is the same as MCSP, have been isolated from a synthetic human scFv library by panning against purified HMW-MAA (Desai, S. A., et al. (1998) *Cancer Res.* 58, 2417-2425). The MCSP molecule is expressed predominantly on the surface of most human melanoma cells, and also on capillary endothelial cells of glial tumors. The finding that MCSP is the cognate antigen for at least two of the melanoma-specific clones isolated from a melanoma patient's scFv fusion-phage library by panning against melanoma cells, suggests that MCSP is a dominant melanoma antigen in vivo.

As an initial test of the therapeutic potential of the two immunoconjugates, an in vitro cytolytic assay involving fluorescent-labeled target cells was used to determine the capacity of the immunoconjugates to target human melanoma cells for lysis by NK cells and by complement. Both of the immunoconjugates produced a sharp increase in the cytolytic activity of NK cells and complement against melanoma cells, resulting in virtually complete lysis of the targeted melanoma cell population and only minor or no increase in lysis of the fibroblast cells used as a control. There was also a significant background of immunoconjugate-independent cytolysis of melanoma cells and fibroblast cells by NK cells and complement, which is expected for an allogenic assay in which the tumor cells, NK cells and complement are isolated from different individuals (Ciccone, E., et al. (1992) *J. Exp. Med.* 175, 709-718). This background should be reduced in a cancer patient, because all of these components are autologous.

The results of the in vitro cytolytic tests provide preliminary evidence that immunoconjugates could have a potential role in immunotherapy protocols with melanoma and other cancers for which tumor-specific scFv or VH targeting domains are available. A limited phase-I clinical trial for melanoma immunotherapy with the mouse mAb 9.2.27, which binds to MCSP, showed specific localization of the antibody in the tumors without evidence of associated toxicity (Oldham, R. K., et al. (1984) *J. Clin. Oncol.* 2, 1235-1244). The scFv immunoconjugates that bind to MCSP should be more effective than a mouse mAb for immunotherapy, because the smaller molecular size should improve tumor penetration, and the human derivation of the molecule should minimize an immune rejection response. The G71-1 and E26-1 immunoconjugates probably bind to different MCSP epitopes, as suggested by major differences in their $V_H$ sequences (see SEQ ID NO: 11 and SEQ ID NO: 12 and the next example), and therefore could be administered together to enhance therapeutic efficacy.

Example 2

This example reports that an immunotherapy treatment for cancer that targets both the tumor vasculature and tumor cells has shown promising results in a severe combined immunodeficient mouse xenograft model of human melanoma. The procedure involved systemic delivery to SCID mice of two immunoconjugates, each composed of a tumor-targeting domain conjugated to the Fc effector domain region of a human IgG1. The effector domain induces a cytolytic immune response against the targeted cells by natural killer (NK) cells and complement. The immunoconjugates are encoded as secreted molecules in a replication-incompetent adenoviral vector.

Materials and Methods. Cell lines. The melanoma cell lines LXSN, TF2 and LXSN/VEGF were derived from the human melanoma line YU-SIT1 by retroviral-mediated transfection and cloning The LXSN line was transfected with the control retrovirus and expresses a low level of TF. The TF2 line was transfected with a retrovirus encoding TF cDNA and expresses a high level of TF. The LXSN/VEGF line was transfected with a retrovirus encoding VEGF cDNA and expresses high level of VEGF. The human kidney line 293 was purchased from the American Type Culture Collection.

Plasmid vector. The construction of the plasmid vector encoding the scFv (G71-1) immunoconjugate was described in Example 1 (see also SEQ ID NO: 11). For the construction of the vector encoding the mouse factor VII (mfVII) immunoconjugate, the mfVII cDNA was amplified by PCR from a mouse liver cDNA library (Quick-Clone cDNA, Clonetech) using the 5'-primer ACGATCTTAAGCTTCCCCA-CAGTCTCATCATGGTTCCA (SEQ ID NO: 7) and the 3'-primer ACGGTAACGGATCCCAGTAGTGG-GAGTCGGAAAACCCC (SEQ ID NO: 8). The amplified mfVII cDNA, which contains the leader and coding sequences without a stop codon, was cloned into the HindIII and BamHI sites of the pcDNA3.1 (+) vector (Invitrogen) in-frame with a cDNA encoding the human IgG1 Fc domain. The vector DNA was amplified in HB101 competent cells (Life Technologies) and sequenced. The active site of mfVII cDNA was mutated by substituting an alanine codon for lysine-341 (Dickinson, C. D., et al. (1996) *Proc. Natl. Acad. Sci. USA* 93, 14379-14384). The mutagenesis procedure was done as described in the QuickChange site-directed mutagenesis manual (Stratagene). The 5'-primer was GGTACCAAG-GACGCCTGCGCGGGTGACAGCGGTGGCCCA (SEQ ID NO: 9) and the 3'-primer was TGGGCCACCGCTGT-CACCCGCGCAGGCGTCCTTGGTACC (SEQ ID NO: 10). The mfVII cDNA with the active site mutation is designated mfVIIasm. The plasmid containing mfVIIasm cDNA was transformed into HB101 competent cells, and transformed colonies were selected on 2×TY/carbenicillin agar. The sequence of the plasmid DNA showed a substitution of an alanine codon (GCG) for the lys-341 codon (AAG) in the mfVIIasm DNA.

Synthesis of immunoconjugates in CHO cells. The procedures for transfecting the immunoconjugate cDNAs into CHO cells and isolating clones were described in Example 1. The transfected CHO cells were cultured in CHO serum-free medium (EX-CELL 301, JRH Biosciences); for synthesis of the mfVIIasm immunoconjugate, the CHO serum-free medium was supplemented with vitamin K1 (Sigma) to a final concentration of 1 µg/ml. The immunoconjugates were purified by affinity chromatography on Protein A beads (Pierce) and were concentrated and desalted by centrifugation through an Ultrafree-15 Biomax-50 filter (Millipore) and adjusted to 10 mM Tris-HCl pH 8.0. The immunoconjugate concentrations were measured by the Bio-Rad protein assay procedure.

Fluorescence-activated cell sorting (FAGS). Melanoma cells were harvested in nonenzymatic dissociation solution (Sigma), washed and resuspended in TBS/BSA/$Ca^{2+}$ (10 mM Tris-HCl pH 7.4, 150 mM NaCl, 20 mM $CaCl_2$, 1% BSA and 0.1% $NaN_3$). An immunoconjugate was added (5 µg/ml final concentration) and the cells were incubated for 30 mM either at 3° C. for the mfVIIasm immunoconjugate or on ice for the G71-1 immunoconjugate; the control cells were incubated without added immunoconjugate. After incubation the cells were washed with TBS/BSA, incubated 30 min on ice with fluorescein-labeled anti-human Fc γ-chain (Vector Laboratories), and analyzed on a Becton-Dickenson FACsort instrument.

Adenoviral vectors. The adenoviral vector system consists of the shuttle vectors pAdTrack-CMV and pShuttle-CMV, and the backbone vector pAdEasy-1 (He, T. C., et al. (1998) *Proc. Natl. Acad. Sci. USA* 95, 2509-2514). The immunoconjugate cDNAs were isolated from the pcDNA3.1 plasmid vectors by digestion with HindIII followed by Klenow fragment to fill-in the 3'-recessed end, and then were digested with NotI to release the cDNA insert which was purified by agarose gel electrophoresis. The shuttle vectors were first digested with KpnI followed by Klenow fragment, and then were digested with NotI. The immunoconjugate cDNAs were ligated into the shuttle vectors by incubation with T4 DNA ligase at 16° C. overnight, and the shuttle vectors were transformed into HB101 competent cells by heat-shock. Transformed colonies were selected on 2×TY/kanamycin agar, and the shuttle vectors were extracted and purified. The purified shuttle vectors and pAdTrack-CMV DNAs were digested with Pme1 at 37° C. for 2 hr. A mixture of 500 ng shuttle vector DNA and 100 ng pAdEasy-1 DNA was electroporated into BJ5183 competent cells, and the cells were shaken at 37° C. for 15 min and plated on LB/kanamycin agar. The plates were incubated at 37° C. overnight, and transformed colonies were isolated. The plasmid DNAs were purified from minipreps and screened for recombinant adenoviral DNA by electrophoresis on 0.6% agarose gels.

The recombinant adenoviral DNAs encoding the immunoconjugates were transfected into $1 \times 10^5$ 293 cells, following the protocol described above for transfecting CHO cells. The cells were collected 7 days after transfection, and the adenoviruses were released by 3 freeze-thaw cycles and amplified by infecting 293 cells in one 150 mm culture plate. After 2 days the adenoviruses were harvested as described above and amplified again by infecting 293 cells in 20 culture plates. The amplified adenoviruses were harvested 2 days later and purified by centrifugation in CsCl. The final yields usually were about $10^{13}$ virus particles as estimated from the absorbance at 260 nm; the conversion is 1 O.D. unit=$1 \times 10^{12}$ particles. The purified adenoviruses were dialyzed against PBS and stored at $-80°$ C.

SCID mice experiments. The SCID mice were 4- to 5-weeks old females from Taconic laboratories. The mice were injected subcutaneously into the right rear flank with $5 \times 10^5$ TF2 or LXSN human melanoma cells. After the tumors had grown to a palpable size below the skin surface (~5 mm$^3$) or to a larger size above the skin surface (~50 mm$^3$), the mice were injected via the tail vein with the adenoviral vector encoding an immunoconjugate, or as a control with the adenoviral vector that does not encode an immunoconjugate. The concentration of immunoconjugate protein secreted into blood was measured by collecting about 0.1 ml of blood from one eye into a microcapillary tube coated with heparin, and centrifuging the blood to remove cells. The supernatant plasma was diluted with sodium bicarbonate buffer pH 9.6 and distributed into wells of pro-bind assay plates (Falcon), and the plates were incubated first at 37° C. for 2 hr and then at 4° C. overnight. The wells were blocked with 5% nonfat milk in PBS for 30 min and washed 3 times with PBS, and a peroxidase-labeled anti-human IgG antibody diluted 1:2000 in 5% nonfat milk was added to the wells. The plates were incubated for 1 hr at room temperature and washed in PBS, and the peroxidase substrate OPD was added and absorbance was measured at 490 nm in a microplate reader. The protein standard was human IgG (Sigma) purified by chromatography on Protein A beads.

The size of a tumor appearing on the skin of a SCID mouse was measured in two dimensions with a caliper, and the tumor volume was estimated by the formula (width)$^2$ (length)/2. At the end of an experiment, the mice were dissected and the tumors were weighed. The organs were examined for morphological evidence of damage, and paraffin sections were prepared for histological examination.

Immunohistochemistry. Paraffin sections of the tumors and organs were incubated in PBS+0.3% $H_2O_2$ for 30 min and blocked in TBS/BSA buffer for 30 min. A solution containing 10 μg/ml of the mfVIIasm immunoconjugate in TBS/BSA/$Ca^{2+}$ buffer, or as a control the buffer without the immunoconjugate, was added to the sections and incubated at 37° C. for 1 hr. After washing 3 times in the same buffer, the sections were incubated at room temperature for 1 hr with anti-human γ-chain antibody labeled with alkaline phosphatase, stained with BCIP/NBT which produces a blue color, and counterstained with methyl green. Results. Properties of the immunoconjugates. The scFv (G71-1) and the mutated mouse factor VII (mfVIIasm) immunoconjugates were synthesized in CHO cells and purified from the culture medium by affinity chromatography on Protein A beads. An earlier analysis by SDS-PAGE showed that the G71-1 immunoconjugate is composed of two identical chains, presumably coupled by disulfide bridges between the hinge regions of the Fc domains (Example 1). The same result was obtained with the mfVIIasm immunoconjugate. (See SEQ ID NO: 11 and SEQ ID NO: 12.) Because the mfVIIasm immunoconjugate has two targeting domains, as compared to the single targeting domain in the monomeric endogenous fVII molecule, it can bind cooperatively to two TF molecules, resulting in stronger binding than endogenous fVII to cells expressing TF. A competitive FACS assay showed that human fVIIa competes on an equimolar basis with the mfVIIasm immunoconjugate for binding to half of the accessible sites on human melanoma cells, probably because only one of the targeting domains on the immunoconjugate molecule can bind to TF at these sites. The binding of the mfVIIasm immunoconjugate to the remaining sites could not be competed in the presence of a tenfold excess of human fVIIa, suggesting that both targeting domains of the immunoconjugate molecule can bind at these sites and provide a strong avidity effect. It appears that only about half of the TF molecules on the melanoma cells are sufficiently close to a second TF molecule to form a cooperative binding site for both targeting domains on a mfVIIasm immunoconjugate.

Figure 4A:
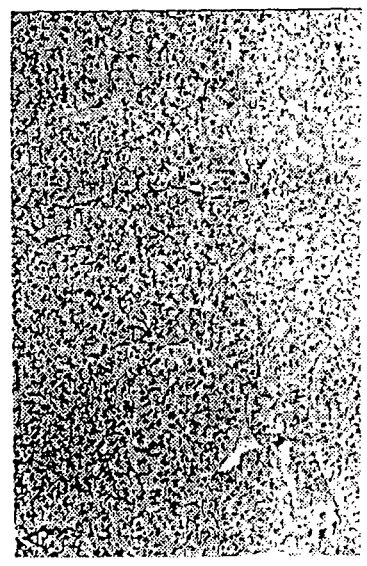
FIG. 4 shows a immunohistochemical assay for binding of a mutated mouse factor VII (mfVIIasm) immunoconjugate to tumor cells and tumor vascular endothelial cells in a human melanoma xenograft grown in SCID mice. The 2nd antibody was anti-human γ-chain labeled with AP, and the AP substrate was BCIP/NBT which produces a blue color; the counterstain was methyl green. Panel A: Control stained with hematoxylin+eosin showing extensive vascularization of the xenograft. Panel B: Immunohistochemistry with the mfVIIasm immunoconjugate showing intense staining of both the vascular endothelial cells and tumor cells. Panel C: Immunohistochemical control without the mfVIIasm immunoconjugate.
Figure 4B:
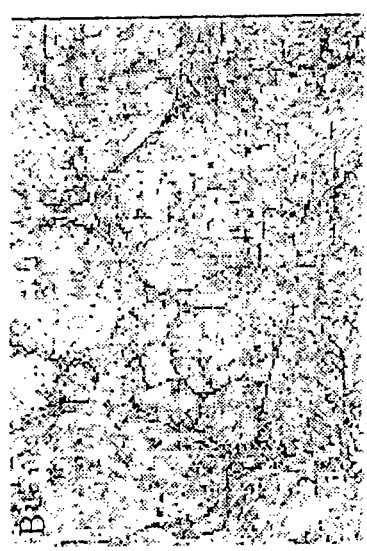
Figure 4C:
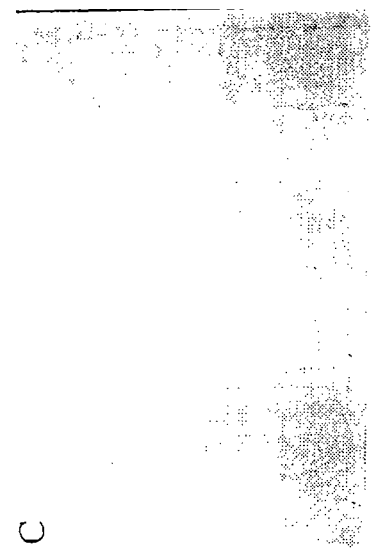

The xenografts for the immunotherapy tests were generated from the human melanoma lines LXSN and TF2 which express, respectively, low or high levels of TF. The mfVIIasm immunoconjugate binds more extensively to the TF2 cells than to the LXSN cells as determined by FACS, consistent with the higher level of TF expression by TF2 cells. The mfVIIasm immunoconjugate was also tested by immunohistochemistry for binding to sections of a human melanoma xenograft generated from the melanoma line LXSN/VEGF which produces a high level of VEGF, resulting in a densely vascularized xenograft. Binding occurred to the tumor vascular endothelial cells as well as to the tumor cells (FIG. 4), indicating that TF is expressed by both cell types in the xenograft. Immunohistochemistry tests with sections of normal mouse liver, kidney, lung and brain showed that the mfVIIasm immunoconjugate does not bind to vascular endothelial cells in these tissues, consistent with other evidence that TF is not expressed by vascular endothelial cells of non-tumorous tissues.

Figure 5A:
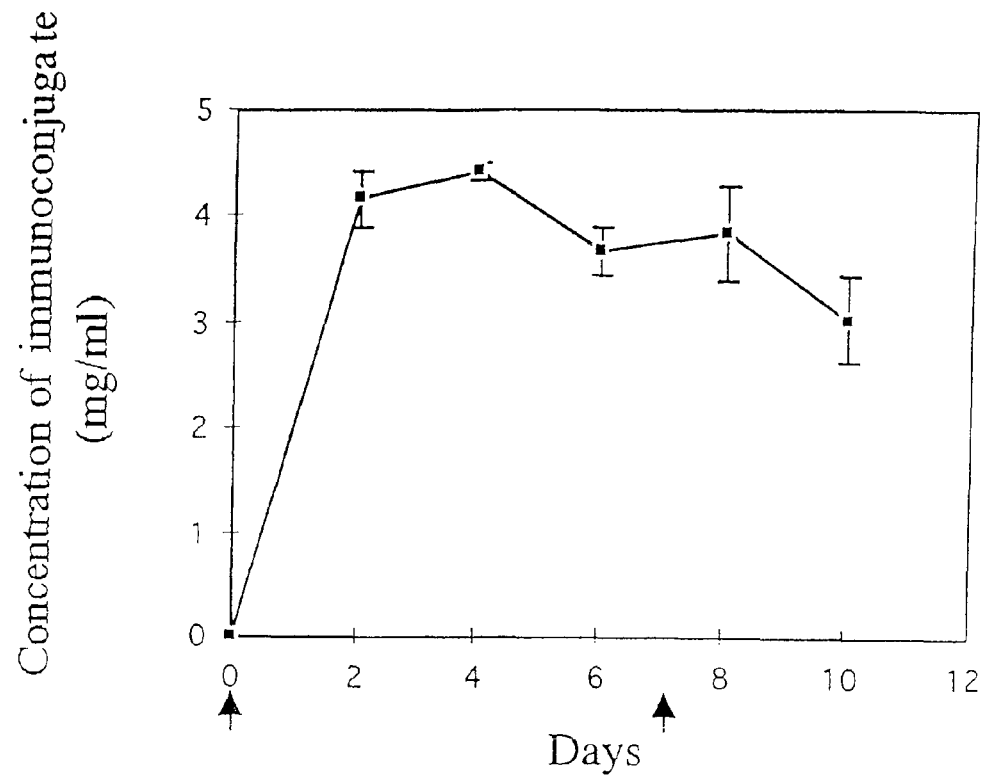
FIG. 5 are line graphs showing concentrations of the G71-1 scFv and mfVIIasm immunoconjugates in the blood of SCID mice after intravenous injections of replication-incompetent adenoviral vectors encoding the immunoconjugates. The mice were injected on day 0 and day 7 with $2\times10^{11}$ adenovirus encoding the G71-1 immunoconjugate (A) or with $4\times10^{11}$ adenovirus encoding the mfVIIasm immunoconjugate (B). The concentration of the encoded immunoconjugate in the blood was determined by ELISA. Each point is the average of the concentration for the 5 mice in each group.
Figure 5B:
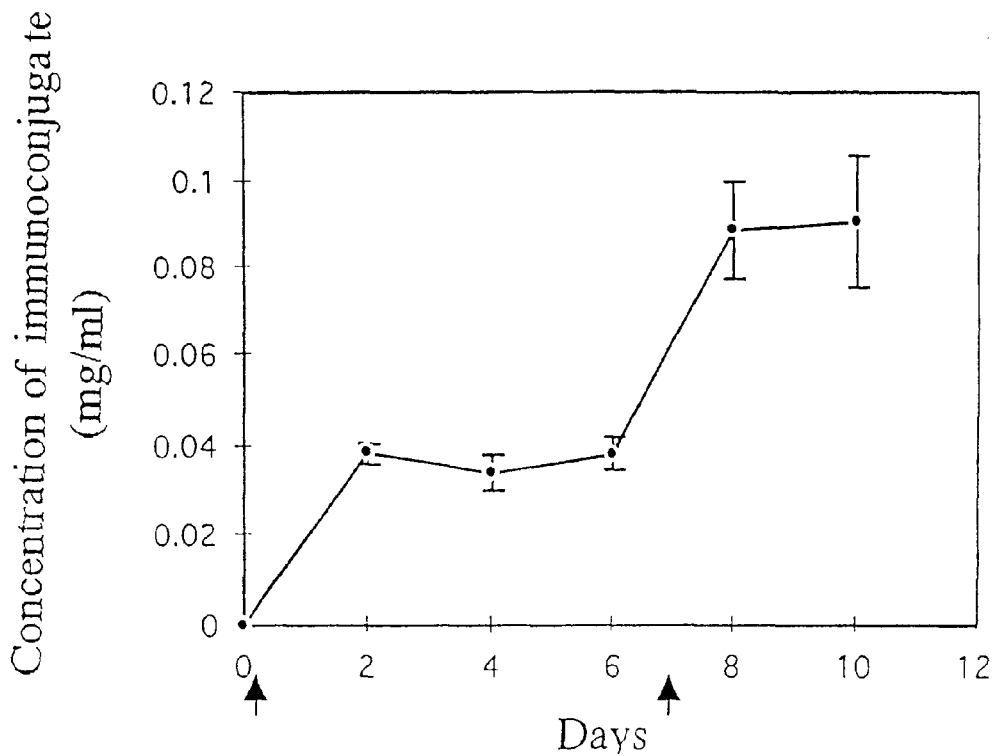
Figure 7:
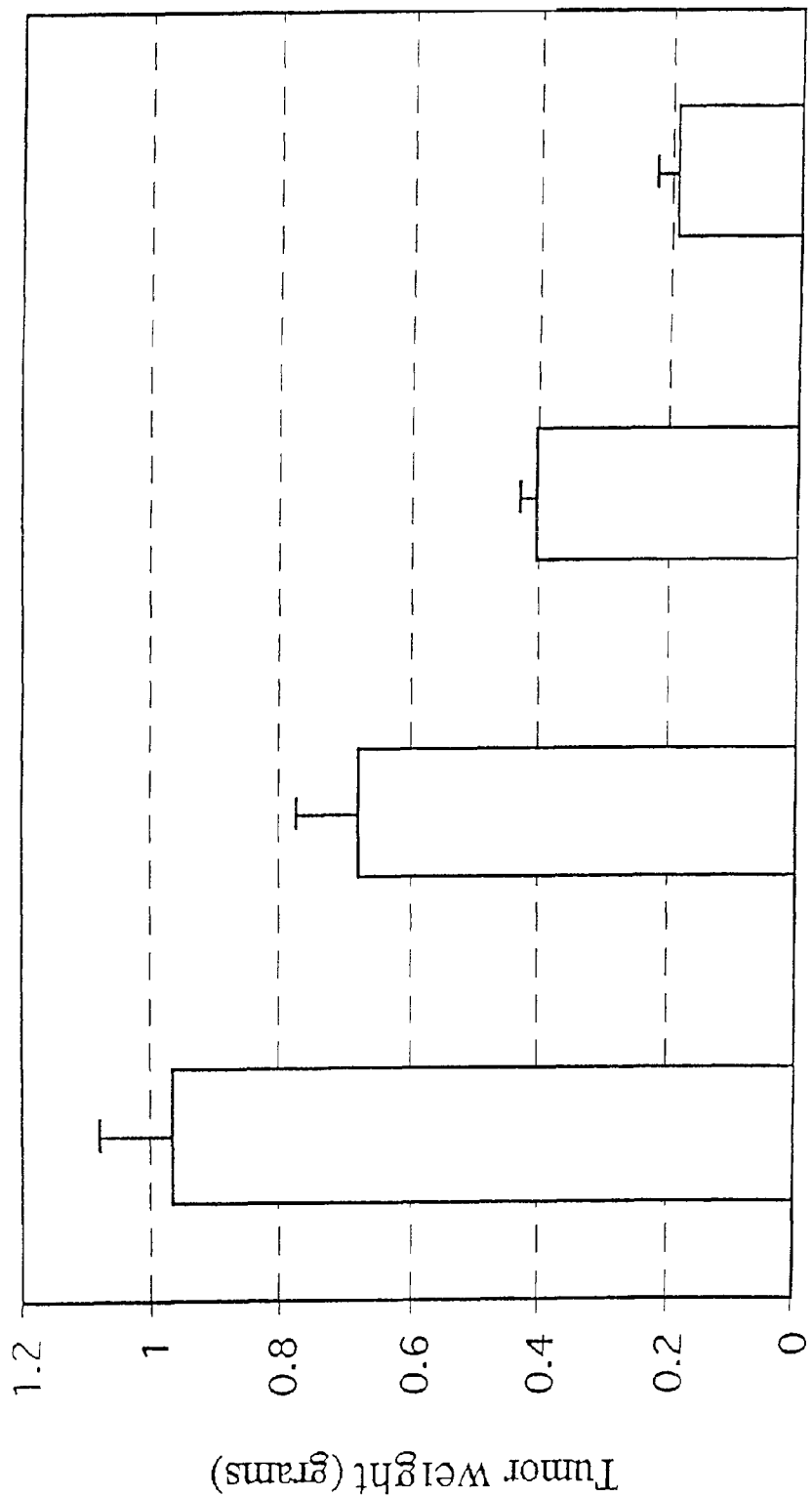
FIG. 7 is a bar graph showing tumor weights of the xenografts from the experiment reported in FIG. 6 and Example 2. The xenografts were dissected from the mice on day 20, which was 6 days after the last injection of adenovirus. The bar heights are the average weights for the 5 mice in each group.

Immunotherapy tests. For systemic delivery to SCID mice, each immunoconjugate was encoded as a secreted molecule in the replication-defective adenoviral vector system based on pAdEasy-1 (He, et al., cited above), and the vectors were injected into the tail vein of mice that had first been injected subcutaneously with human melanoma cells. The initial immunotherapy tests involved injecting each vector separately, and both vectors together, into the mice that had developed a palpable TF2 xenograft. A total of three injections were administered at weekly intervals, and the experiment was terminated 6 days after the last injection. The concentration of the immunoconjugates in the blood was monitored by ELISA after the first and second injections (FIG. 5). The average concentration after the first injection was 4 mg/ml for the G71-1 immunoconjugate and 0.04 mg/ml for the mfVIIasm immunoconjugate, indicating that the rate of synthesis was about 100-fold higher for the G71-1 immunoconjugate than for the mfVIIasm immunoconjugate. The concentration of each immunoconjugate increased after the second injections, indicating that additional cells had been infected by the adenoviruses. The growth of the xenografts was monitored by measuring in two dimensions the size of the tumor appearing on the skin surface, and using the measurements to estimate the tumor volume (FIG. 6). In the control mice injected with the adenovirus that does not encode an immunoconjugate, the tumor grew continuously at a relatively fast rate, reaching an average volume of about 2,000 mm$^3$ after 20 days. In the mice injected with an adenovirus encoding an immunoconjugate, tumor growth was inhibited; the inhibition was stronger for the mfVIIasm immunoconjugate than for the G71-1 immunoconjugate. All of the mice remained active and appeared healthy at the end of the experiment, and histological examination of the liver, spleen, lung, kidney and brain did not show any evidence of necrosis, clotting or bleeding. The tumor weights after autopsy were lower in the mice treated with the immunoconjugates than in the control mice, consistent with the estimated tumor volumes (FIG. 7). The strongest reduction of tumor weight occurred in the mice treated with both immunoconjugates.

Figure 8:
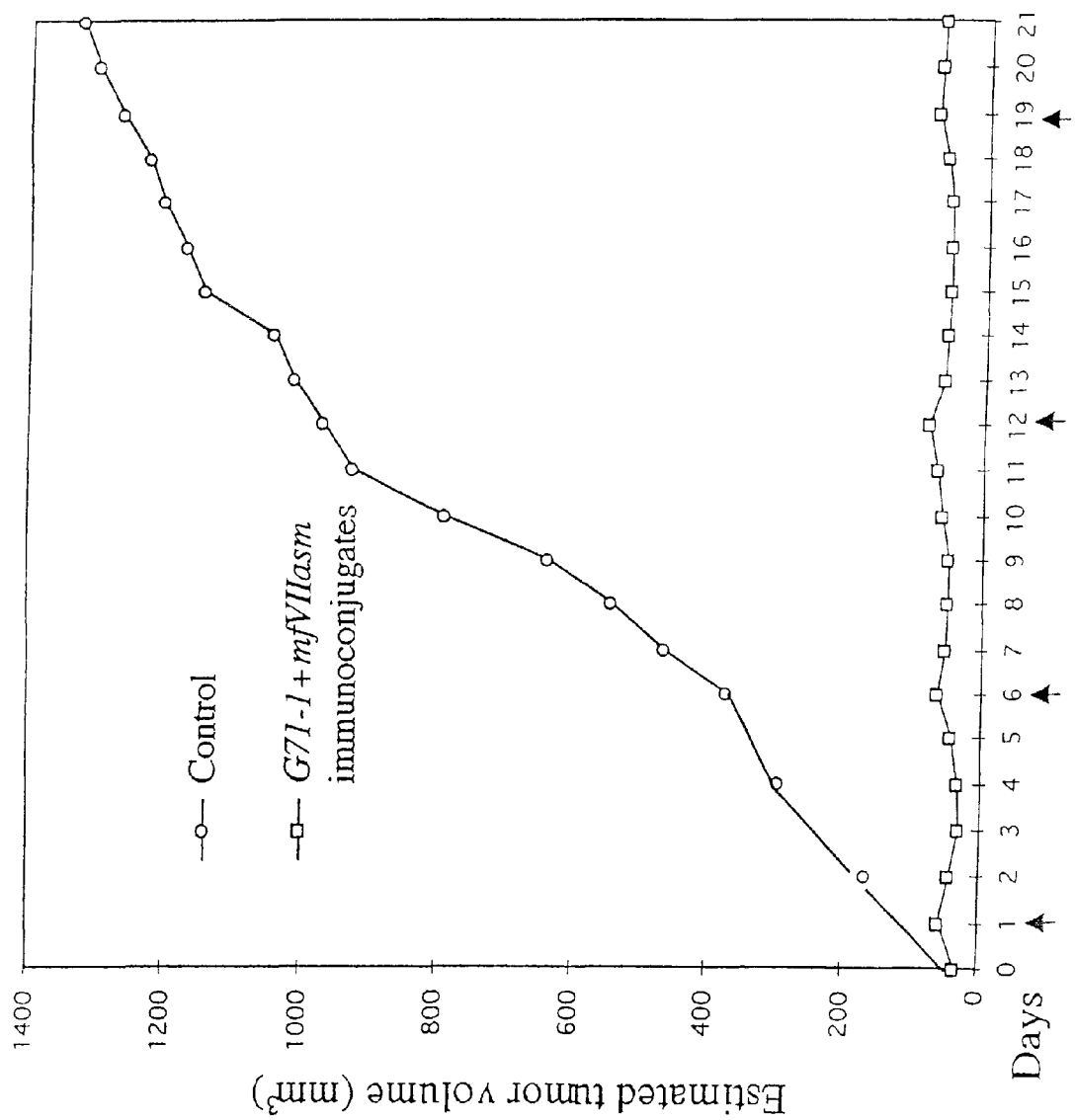
FIG. 8 is a line graph showing the inhibitory effect of the G71-1 and mfVIIasm immunoconjugates on the growth of a large human melanoma xenograft in SCID mice. Each mouse was injected subcutaneously with $5\times10^5$ melanoma cells, and the xenografts were allowed to grow to an estimated tumor volume of 50 mm$^3$ on the skin surface (day 1). A mixture of $2\times10^{11}$ adenoviruses encoding the G71-1 immunoconjugate and $7\times10^{11}$ adenoviruses encoding the mfVIIasm immunoconjugate was injected into the tail vein of 5 mice on days 1, 6, 12 and 19. As a control 5 mice were injected with $4\times10^{11}$ adenoviruses that did not encode an immunoconjugate. The estimated tumor volumes are the averages for the 5 mice in each group. One of the mice injected with the adenoviruses encoding the immunoconjugates was found dead on day 17.

The next two experiments were designed to test two parameters that could affect the therapeutic efficacy of the immunoconjugates, namely the initial size of the xenograft and the level of TF expression by the melanoma cells. (i) The preceding immunotherapy tests involved palpable melanoma xenografts that had grown to an estimated volume of about 5 mm$^3$, corresponding to a small tumor in humans. To test the therapeutic efficacy of the immunoconjugates against a larger xenograft, TF2 xenografts were allowed to grow to an estimated volume of about 50 mm$^3$ before starting tail vein injections of the two adenoviral vectors. The mice received 4 injections during a period of 3 weeks, and the experiment was terminated 2 days after the last injection. The average tumor volume in the mice injected with the adenoviruses encoding the immunoconjugates was about the same at the end as at the start of the experiment, in contrast to the average tumor volume in the mice injected with the control adenovirus which increased by a factor of about 27 during the same period (FIG. 8). These results show that tumor growth is inhibited as effectively with the larger tumor as with the smaller tumor. One of the 5 mice injected with the adenovirus encoding the immunoconjugates died 5 days after the third injection; the cause of death could not be determined because the mouse was not recovered in time for examination. (ii) A parameter that might affect the efficacy of the mfVIIasm immunoconjugate is the level of TF expression, which varies among different tumors (Callender, N. S., et al. (1992) Cancer 70, 1194-1201). To study the effect of varying the expression of TF by the melanoma cells in a xenograft, the melanoma line LXSN was used to generate a xenograft expressing a low level of TF, for comparison with the xenograft generated from the related line TF2 which expresses a higher level of TF (Bromberg, M. E., et al. (1999) Proc. Natl. Acad. Sci. USA 92, 8205-8209). After the xenografts reached a palpable size, the mice received during the next 3 weeks 5 injections of the adenovirus encoding the fVIIasm immunoconjugate or the control adenovirus (FIG. 11). In the 5 mice injected with the control adenovirus the xenograft grew continuously, the average volume increasing to 1350 mm$^3$ on the second day after the last injection. During the same period the average volume of the xenografts in the mice injected with the mfVIIasm immunoconjugate increased to 20 mm$^3$, indicating that the inhibition of tumor development is comparable for the LXSN and TF2 xenografts (compare FIGS. 9 and 6). The autopsies performed one day after the last injection showed that the xenograft had been eradicated in 2 of the 5 mice injected with the adenovirus encoding the mfVIIasm immunoconjugate; the average tumor weight in the other 3 mice was 0.11 gm as compared to the average weight of 0.75 gm in the 5 mice injected with the control adenovirus. The small tumors recovered from these 3 mice showed extensive regions of cell necrosis, which did not occur in the larger tumors from the control mice (FIG. 10). All of the mice appeared healthy at the end of this experiment, but a morphological examination of the dissected mice revealed damage to the liver and spleen in the 5 mice injected with the adenovirus encoding the mfVIIasm immunoconjugate. Histological examination of the liver and spleen showed that many of the liver cells were enlarged and the spleen was extensively infiltrated with erythrocytes. Enlarged liver cells also occurred in a previous experiment after 3 injections of the adenovirus encoding the mfVIIasm immunoconjugate, but the spleen was normal, indicating that the defects in the spleen developed in the course of the last 2 injections. One of the mice also had a subdural brain hemorrhage, which did not occur in other mice from this experiment or any of the previous experiments. It is uncertain whether this defect was induced by the binding of the mfVIIasm immunoconjugate to TF expressed in the brain vasculature, or occurred spontaneously.

Discussion. The immunotherapy procedure in this example involved systemic delivery to SCID mice of two immunoconjugates, each composed of a tumor-targeting domain conjugated to the Fc region of a human IgG1 heavy-chain, forming a homodimeric molecule similar to a Camelid heavy-chain antibody. For one type of immunoconjugate, the tumor-targeting domain was the human scFv molecule G71-1 that binds to the melanoma antigen MCSP expressed by the melanoma cells in the xenografts. For the other type of immunoconjugate, the tumor-targeting domain was a mouse factor VII molecule that binds specifically and tightly to tissue factor (TF), both to mouse TF expressed by the tumor vasculature endothelial cells and to human TF expressed by the melanoma cells in the xenografts. To decrease the risk of disseminated intravascular coagulation (DIC) that might result from the binding of a factor VII immunoconjugate to TF, an active site mutation was introduced into the mouse fVII targeting domain (mfVIIasm), inhibiting the proteolytic activity required to initiate the blood coagulation pathway.

The study reported in Example 1 showed that the G71-1 immunoconjugate mediates cytolysis of cultured human melanoma cells by NK cells and complement. Because SCID mice retain the capacity to produce functional NK cells and complement, the immunoconjugates could also mediate cytolysis of the targeted tumor cells and vascular endothelial cells of a human melanoma xenograft growing in SCID mice. Systemic delivery of the immunoconjugates to SCID mice was achieved by tail vein injections of a replication-defective adenoviral vector encoding the immunoconjugates, which were secreted into the blood for at least one week after each injection. The mice first were injected subcutaneously with a human melanoma cell line that expresses either a low or high level of TF, and the resulting xenograft was allowed to grow into a small (~5 mm$^3$) or larger (~50 mm$^3$) tumor before starting injections of the adenoviral vectors. Further growth of all the xenografts was prevented for the 3 to 4 week period of the experiments by multiple injections of the adenovirus encoding the mfVIIasm immunoconjugate, administered separately or together with the adenovirus encoding the G71-1 immunoconjugate; in some of the mice the xenograft completely regressed. In the control mice, which were injected with an adenovirus that did not encode an immunoconjugate, the average volume of the xenografts increased by a factor of about 25 during the same period. In the mice receiving 5 injections of the adenoviral vectors encoding the immunoconjugates, many of the liver cells were enlarged and the spleen was infiltrated with erythrocytes. The defects were not caused by the secreted immunoconjugates, which do not bind to the liver or spleen cells. The primary cause probably is the continuous high level synthesis of the encoded immunoconjugates by the liver cells, which are the mouse cells predominately infected by intravenously-injected adenoviral vectors. Although the immunoconjugate concentration in the blood of SCID mice injected with an adenoviral vector was about 100-fold higher for the G71-1 immunoconjugate than for the mfVIIasm immunoconjugate, the inhibitory effect on a human melanoma xenograft nevertheless was stronger with the mfVIIasm immunoconjugate. A key advantage of the mfVIIasm immunoconjugate is the binding that occurs to tumor vascular endothelial cells as well as to tumor cells, in contrast to the G71-1 immunoconjugate which binds only to melanoma cells. The binding to the tumor vasculature should be tumor-specific, because TF is not expressed by the normal vasculature. Although TF is expressed by several other normal tissues, such as brain, lung and kidney glomeruli, these TF molecules are not accessible to endogenous fVII or a fVII immunoconjugate because the blood vessel walls form a barrier separating larger blood components from adjacent cells. However, tumor blood vessels are leaky, allowing access to TF expressed by tumor cells. Thus, a human fVIIasm immunoconjugate can be an effective therapeutic agent for a broad spectrum of human tumors expressing TF on the vascular endothelial cells and tumor cells. The therapeutic efficacy of a human fVIIasm immunoconjugate can be enhanced by also administering a human scFv immunoconjugate that binds to a tumor cell target other than TF.

Example 3

This example reports a study of the efficacy and safety of a protocol for cancer treatment tested in a SCID mouse model of human skin and metastatic lung melanoma, and in an immunocompetent mouse model of mouse melanoma. The protocol involved intratumoral injections of replication-incompetent adenoviral vectors encoding immunoconjugates of the invention that elicit a cytolytic immune response against the targeted neovasculature endothelial cells and tumor cells. The mouse model experiments showed that intratumoral delivery of the factor VII immunoconjugate, either alone or together with the single-chain Fv immunoconjugate, resulted in growth inhibition and regression of the injected tumor, and also of distant uninjected metastatic tumors, without evidence of damage to normal organs. There was extensive destruction of the tumor neovasculature, presumably mediated by the factor VII immunoconjugate bound to tissue factor on neovasculature endothelial cells. Because tissue factor is generally expressed on neovascular endothelial cells and tumor cells, a factor VII immunoconjugate can be used for immunotherapy against a broad range of human tumors.

Materials and Methods. Cell lines. LXSN, TF2 and Yusac2 are human melanoma lines, Caki is a human renal tumor line, LnCap is a human prostate tumor line, A204 is a human neuroblastoma line, B16F10 is a mouse melanoma line, EMT6 is a mouse mammary tumor line, BT20 is a human breast tumor line, Colo 357 is a human pancreatic tumor line, MS is a human gastric tumor line, and 293 is a human kidney line (ATCC, CRL-1573) used for packaging the adenoviral vectors. The culture medium was DMEM+10% FBS for all of the tumor lines except LnCap, which was cultured in RPMI 1640+10% FBS.

Adenoviral vectors. 1) Procedures summarized in Example 2 above for producing and purifying the adenoviral vectors encoding the mfVIIasm and G71-1 immunoconjugates were used with the following modification. After the shuttle vector DNAs were digested with PmeI, instead of an ethanol precipitation step the DNAs were purified by electrophoresis in agarose gel followed by isolation of the DNA bands using the QIAEX II kit (Qiagen). 2) The vector concentrations in the purified preparations were determined by assays for infectious particles (IP) and infectious units (IU), as follows. (i) The IP assay involves diluting the vector preparation 20-fold in lysis buffer (0.1% SDS in PBS) and measuring absorbance at 260 nm; the conversion to IP is 1 O.D. unit=$1 \times 10^{12}$ IP. (ii) The IU assay involves infecting cultures of 293 cells with serial dilutions of the vector preparation, incubating the infected cultures for 2 days, and examining the cells in a fluorescence microscope for expression of the Green Fluorescent Protein (GFP) gene in the vector genome. The IU titer is calculated from the number of cells expressing the GFP gene. The IP and IU titers agreed within ±10%.

Synthesis of the mfVIIasm immunoconjugate in tumor cells. Tumor cells were grown almost to confluence in 150-mm dishes, and the cells were infected with the adenovirus encoding the mfVIIasm immunoconjugate at a multiplicity of 10 IU per cell. The infected cells were cultured in serum-free medium for 4 days, and 1.5 ml of the medium was mixed with 10 µl of a suspension of protein-A beads (Pierce) and rotated at 4° C. overnight. The bound mfVIIasm immunoconjugate was eluted by heating the beads in 15 µl of SDS-PAGE loading buffer at 80° C. for 3 min, and the eluate was fractionated by SDS-PAGE and transferred to a nitrocellulose membrane. The immunoconjugate band was detected by immunostaining with a goat anti-human or anti-mouse IgG (Fc specific) probe.

Immunotherapy tests in immunodeficient mice. Female C.B-17 SCID mice 4- to 5-weeks old (Taconic Farms) were used for all experiments with immunodeficient mice. Monolayer cultures of the human melanoma lines LXSN or TF were dissociated in PBS+2 mM EDTA, washed and resuspended in PBS. Skin tumors were generated by subcutaneous injections of $5 \times 10^5$ cells into the right rear flank, and metastatic lung tumors were generated by intravenous injections of $6 \times 10^5$ TF cells into the tail vein. The size of the skin tumor was measured in two dimensions with a caliper, and the tumor volume was estimated as (width)$_2$ (length)/2. When a skin tumor had grown to a volume of about 100 mm3, intratumoral injections of an adenoviral vector containing a human Fc effector domain was started. For each injection step, a total volume of 50 µl of the vector preparation was injected into 3 or 4 sites on the tumor. At the end of the experiment, autopsies were done to collect blood samples and to prepare the tumors and normal organs for morphological and histological examination. Immunotherapy tests in immunocompetent mice.

Female C57BL/6 mice 4- to 5-weeks old (Charles River Laboratories) were used for all experiments involving immunocompetent mice. Monolayer cultures of B16F10 mouse melanoma cells were suspended in PBS+2 mM EDTA, washed and resuspended in PBS. Skin tumors were generated by subcutaneous injections of $5\times10^5$ cells into the right rear flank. When the skin tumors had grown to an estimated volume of 140 to 325 mm$^3$, tail vein injections of the adenoviral vector encoding the mfVIIasm immunoconjugate containing a mouse Fc effector domain were started. The procedures for monitoring the efficacy and safety of the protocol are the same as described above for SCID mice.

SGOT assays. Serum samples were collected from mice, frozen and assayed for glutamic oxalacetic transaminase using a standard diagnostic kit.

Results. The two immunoconjugates used for this study are composed of a tumor-targeting domain and an effector domain (FIG. 1). The targeting domain is either a mutated mouse factor VII molecule (mfVIIasm) that binds to TF expressed on tumor vascular endothelial cells and tumor cells but does not initiate blood coagulation (Example 2), or the scFv antibody G71-1 that binds to its cognate antigen expressed selectively on human melanoma cells (Cai and Garen, cited above, and Example 1). The effector domain is the Fc region of a human or mouse IgG1 immunoglobulin that induces a cytolytic immune response against the targeted cells (Example 1). The vector for delivering the immunoconjugates is a replication-incompetent adenovirus encoding a secreted form of the immunoconjugates (Example 1). In Example 1, intravenous injections into SCID mice of the vectors encoding the immunoconjugates inhibited tumor growth but caused histological damage to the liver, which is the primary target for infection by the intravenously injected vector. In order to determine whether the primary infection could be redirected from liver cells to tumor cells, the vectors were injected intratumorally into a human skin melanoma growing in SCID mice, and the distribution of the vector in the tumor and liver was mapped by the expression of the Green Fluorescent Protein (GFP) gene inserted into the vector genome (FIG. 14). Intense GFP expression was detected in the tumor but not in the liver, indicating that an injected tumor is the primary target for infection by the vector. The pattern of GFP expression in the tumor appeared to be restricted to a few layers of tumor cells adjacent to the path traversed by the injection needle.

The effect of vector dose on tumor growth was tested by injecting a mixture of the two vectors encoding the mfVIIasm and G71-1 immunoconjugates, into a human melanoma skin tumor growing in SCID mice, and measuring the tumor volume during the next 5 days. The ratio of the mfVIIasm vector to the G71-1 vector in the mixture was 5 to 1, in order to compensate for the higher titer of the G71-1 immunoconjugate secreted into the blood (Example 2). The combined dose of the two vectors used for the injections was varied from $7\times10^8$ to $6\times10^9$ infectious units (IU). For a control, an empty vector without an encoded immunoconjugate was injected at a dose of $6\times10^9$ IU. The strongest inhibition of tumor growth was obtained with the highest dose of the vectors encoding the immunoconjugates. This vector dose was used for all of the following SCID mouse experiments.

In the next experiment, the inhibitory effect on tumor growth of administering multiple intratumoral injections of the two vectors encoding the mfVIIasm and G71-1 immunoconjugates was monitored for 19 days. The titer of immunoconjugate proteins in the blood of the mice 2 days after the last injection of the adenoviral vectors ranged from 1 mg/ml to 2 mg/ml, which is about one-fourth the titer produced by intravenously injected vectors (Example 2). The average volume of these tumors decreased by about 70% within one day after the first injection of the two vectors, and the volumes did not subsequently increase during the rest of the experiment. Tumors injected with an empty control vector grew continuously, reaching at the end of the experiment an average volume of 1900 mm$^3$ as compared to 30 mm$^3$ for the tumors injected with the vectors encoding the two immunoconjugates. Tumors injected only with the vector encoding the mfVIIasm immunoconjugate were inhibited almost as strongly as the tumors injected with both vectors, consistent with earlier experiments involving intravenous injections of the vectors (Example 2). The mice remained active throughout the experiment, and in autopsies performed 2 days after the final injections all of the organs appeared morphologically and histologically normal and there was no evidence of bleeding. Because SCID mice injected intravenously with the vectors encoding the immunoconjugates showed histological damage to the liver cells (Example 2), the livers of the SCID mice injected intratumorally were tested for histological and also functional damage. In contrast to the major histological changes seen in liver sections from the intravenously injected mice, liver sections from the intratumorally injected mice showed relatively minor changes (FIG. 15). Liver function was monitored by assays for the enzyme glutamic oxalacetic transaminase (SGOT) in sera obtained from the mice during autopsy. The levels of SGOT in the control mice and the mice injected with the vectors encoding the immunoconjugates remained within the normal range (210±28 U/L), indicating that liver function was not impaired.

The tumors recovered from the mice injected with the vectors encoding the mfVIIasm and G71-1 immunoconjugates were almost completely devoid of blood vessels (FIG. 13), presumably as the result of a cytolytic immune response against vascular endothelial cells induced by the mfVIIasm immunoconjugate bound to TF.

The efficacy of the intratumoral injection protocol depends not only on inhibition of the injected skin tumor but also of metastatic tumors that are not accessible for injection. To test for an inhibitory effect on metastatic tumors, we used a SCID mouse model in which human melanoma TF cells are injected into the tail vein, resulting in blood-borne metastases mainly to the lungs. The mice also were injected subcutaneously with human melanoma LXSN cells at the same time, and the skin tumors that formed 12 days later were injected with the vectors encoding the two immunoconjugates or with an empty control vector. The intratumoral injections were continued on a biweekly schedule for the next 8 weeks, and autopsies were performed 2 days after the last injection to determine the number of tumor nodules on the surface of the lungs (Table 2). The two mice injected with the control vector had 14 and 29 lung nodules, respectively, in contrast to the five mice injected with the vectors encoding the two immunoconjugates, three of which had no lung nodules and two had 1 and 5 nodules, respectively. These results indicate that intratumoral injections of the vectors encoding the two immunoconjugates can inhibit growth of distant metastatic tumors as well as the injected tumor.

TABLE 2

Inhibition of metastatic lung tumors by intratumoral injections of adenoviral vectors encoding the immunoconjugates.

| Adenoviral vectors | Number of metastatic lung tumors |
|---|---|
| Control | 14, 29 |
| Encoding the immunoconjugates | 1, 5, 0, 0, 0 |

SCID mice were injected on day 0 with human melanoma cells intravenously to generate blood-borne metastatic lung tumors and subcutaneously to generate a skin tumor. Intratumoral injections of the adenoviral vectors encoding the mfVIIasm and G71-1 immunoconjugates into the skin tumor was started on day 10, and additional injections were done biweekly for 7 weeks. The autopsies were done 2 weeks after the last injection. The number of mice was 2 for the control vector and 5 for the vector encoding # the immunoconjugates.

Another parameter that could affect the efficacy of the protocol in a clinical setting is a patient's immune response to the immunoconjugates or the adenoviral vector. Because the targeting and effector domains of immunoconjugates for clinical use would be derived from human proteins, patients should not mount a significant immune response to the immunoconjugates. However, the adenoviral vector is strongly immunogenic in humans and also in mice. To assess the effect of an immune response to the adenoviral vector in mice, the protocol was tested in immunocompetent mice carrying a mouse melanoma skin tumor. The experiment involved intravenous instead of intratumoral injections of the vector, because the mouse melanoma cells cannot be infected by the vector. Also, only the mfVIIasm immunoconjugate could be tested, because the mouse melanoma cells bind the mfVIIasm immunoconjugate but not the G71-1 immunoconjugate. The Fc effector domain of the immunoconjugate for this experiment was derived from a mouse IgG1 immunoglobulin. The results show that intravenous injections of the adenoviral vector encoding the mfVIIasm immunoconjugate results in growth inhibition of a melanoma tumor in immunocompetent mice as well as in SCID mice (FIG. 16).

Because TF is generally expressed by tumor vascular endothelial cells and also by most metastatic tumor cells, a fVIIasm immunoconjugate could mediate a cytolytic immune response not only against human melanomas but also against a broad spectrum of other human tumors. As shown in the study reported here, intratumoral injections of an adenoviral vector encoding the mfVIIasm immunoconjugate into a human tumor appears to be a safe and effective protocol for establishing and maintaining a high blood titer of the immunoconjugate. However, the cells of the injected tumor must be susceptible to infection by the adenovirus and be capable of synthesizing and secreting the encoded immunoconjugate. A panel of human and mouse tumor lines, consisting of human melanoma, prostate cancer, breast cancer, pancreatic cancer, renal cancer, gastric cancer, and neuroblastoma lines and mouse melanoma and breast cancer lines, was tested as a host for the adenoviral vector encoding the mfVIIasm immunoconjugate. All of the human tumor lines produced and secreted about the same amount of the immunoconjugate protein, indicating that the intratumoral injection protocol could also be used for other types of human solid tumors in addition to melanoma. The mouse tumor lines failed to produce the immunoconjugate protein, probably because the mouse cells were not infected by the adenoviral vector.

Discussion. The cancer immunotherapy protocol described in this example involves intratumoral injections of replication-incompetent adenoviral vectors encoding immunoconjugate molecules that mediate a cytolytic immune response against the tumor vasculature and tumor cells (FIG. 1). The cells infected by the vectors synthesize the encoded immunoconjugates, which are secreted into the blood and bind to the cognate targets on tumor vasculature endothelial cells and tumor cells. Intratumoral injection of the vectors provides an important safety advantage over intravenous injection, because the vector infects predominantly the cells of the injected tumor instead of liver cells. Neither the liver nor any other organ of the mice showed significant damage from repeated intratumoral injections. Several types of human tumor cells other than melanoma also can be infected by the vector and can synthesize and secrete the encoded immunoconjugate. Thus, the intratumoral injection route for the vectors could be generally applicable to human solid tumors. If no tumor is accessible for injection, the vector could be injected into a susceptible normal tissue.

The therapeutic efficacy of the intratumoral injection protocol was tested in a SCID mouse model of human skin melanoma and metastatic lung melanoma. The tests involved two immunoconjugates containing different targeting domains. 1) One targeting domain is the blood zymogen factor VII (fVII) that binds with high affinity and specificity to the transmembrane receptor tissue factor expressed by endothelial cells of growing blood vessels, including the vessels of the tumor neovasculature, and also by most human tumor cells. A fVII immunoconjugate must compete in vivo with endogenous factor VII for binding to tissue factor on the targeted cells. This competition strongly favors the homodimeric immunoconjugate molecule (FIG. 1) over the monomeric endogenous molecule, because the avidity effect of two targeting domains enhances binding to cells expressing multiple copies of tissue factor (Example 2); also, the blood titer is higher for the vector-encoded fVII immunoconjugate than for endogenous factor VII. A mouse fVII targeting domain was used for the experiments involving human tumor xenografts growing in SCID mice, because it binds tightly both to human tissue factor on the tumor cells and to mouse tissue factor on the mouse endothelial cells in the tumor vasculature. To prevent initiation of the blood coagulation pathway by the binding of a fVII immunoconjugate to tissue factor, which could cause disseminated intravascular coagulation, a mutation was introduced into the active site of the mouse fVII targeting domain (mfVIIasm). 2) The second targeting domain is the single-chain Fv (scFv) antibody G71-1 that binds to a chondroitin sulfate proteoglycan expressed selectively by human melanoma cells (Examples 1 and 2). The results of the immunotherapy tests showed that intratumoral injections of the vector encoding the mfVIIasm immunoconjugate, either alone or together with the vector encoding the G71-1 immunoconjugate, inhibited growth of the injected skin tumor and also of metastatic lung tumors (FIG. 16 and Table 2). The residual tumor tissue remaining after intratumoral injections of the vectors encoding the immunoconjugates was almost devoid of blood vessels (FIG. 13), indicating that the mfVIIasm immunoconjugate induces a potent cytolytic immune response resulting in extensive destruction of the tumor neovasculature.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The papers, patents, and applications cited herein and the references cited in them are expressly incorporated in their entireties by reference.

The invention claimed is:

1. A method for reducing neovasculature in a vascularized tumor, wherein the method comprises: administering to a patient having the vascularized tumor an effective amount of a composition of comprising a conjugate protein having as an effector domain a human IgG1 immunoglobulin Fc domain, said effector domain conjugated to a targeting domain comprising a mutant form of human factor VII comprising the amino acid sequence encoded by the nucleotide sequence at positions 202-1419 of SEQ ID NO: 12, whereby neovasculature in the vascularized tumor is reduced.

2. A method of inhibiting growth of a vascularized tumor, comprising: administering to a patient having the vascularized tumor an effective amount of a composition comprising an immunoconjugate protein comprising a human IgG1 immunoglobulin Fc domain conjugated to a mutant form of human factor VII comprising the amino acid sequence encoded by the nucleotide sequence at positions 202-1419 of SEQ ID NO: 12, whereby growth of the vascularized tumor is inhibited.

3. The method of claim 1 or 2 wherein the step of administering is via intratumoral injection.

4. The method of claim 1 or 2 wherein the step of administering is intravenous.

* * * * *